US010292989B2

(12) United States Patent
Jevtovic-Todorovic et al.

(10) Patent No.: US 10,292,989 B2
(45) Date of Patent: May 21, 2019

(54) GENERAL ANESTHETICS THAT ARE NOT NEUROTOXIC

(71) Applicants: Vesna Jevtovic-Todorovic, Charlottesville, VA (US); Slobodan Todorovic, Charlottesville, VA (US)

(72) Inventors: Vesna Jevtovic-Todorovic, Charlottesville, VA (US); Slobodan Todorovic, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 15/129,539

(22) PCT Filed: Mar. 30, 2015

(86) PCT No.: PCT/US2015/023320
§ 371 (c)(1),
(2) Date: Sep. 27, 2016

(87) PCT Pub. No.: WO2015/149066
PCT Pub. Date: Oct. 1, 2015

(65) Prior Publication Data
US 2017/0173048 A1   Jun. 22, 2017

Related U.S. Application Data

(60) Provisional application No. 61/971,589, filed on Mar. 28, 2014.

(51) Int. Cl.
| A61K 31/568 | (2006.01) |
| A61K 31/56 | (2006.01) |
| A61K 31/565 | (2006.01) |
| A61K 31/58 | (2006.01) |

(52) U.S. Cl.
CPC ............ *A61K 31/568* (2013.01); *A61K 31/56* (2013.01); *A61K 31/565* (2013.01); *A61K 31/58* (2013.01)

(58) Field of Classification Search
CPC .................................................. A61K 31/568
See application file for complete search history.

(56) References Cited

U.S. PATENT DOCUMENTS

| 5,439,900 | A | * | 8/1995 | Bukusoglu | ........... | A61K 31/568 |
| | | | | | | 514/170 |
| 7,098,200 | B2 | | 8/2006 | Brandt et al. | | |
| 2003/0069318 | A1 | | 4/2003 | Dang et al. | | |
| 2009/0061024 | A1 | * | 3/2009 | Eppler | .................. | A61K 31/675 |
| | | | | | | 424/718 |
| 2012/0316247 | A1 | * | 12/2012 | Xie | ......................... | A61K 31/03 |
| | | | | | | 514/722 |

OTHER PUBLICATIONS

Nakashima, Molecular pharmacolumnogy (1998), 54(3), 559-68.*
Shu, British Journal of Pharmacology (2012) 165 2228-2243.*
Han Journal of Medicinal Chemistry (1996), 39(21), 4218-4232.*
Joksovic, Ann. N.Y. Acad. Sci. 1122: 83-94 (2007).*
Sculptoreanu, Molecular and Cellular Biochemistry (2000), 203(1 &2), 23-31.*
Ansel, Pharmaceutical Dosage Forms and Drug Delivery Systems, 1999.*
Holzki, Korean J Anesthesiol May 2011 60(5): 313-322.*
Fodale, Expert Opinion on Drug Safety, 2017 Drug Safety, 2017 vol. 16, No. 9, 997-1008.*
Perouansky, Anesthesiology, Dec. 2009 ; 111(6): 1365-1371.*
Todorovic, et al., "5beta-Reduced Neuroactive Steroids are Novel Voltage-Dependent Blockers of T-Type Ca2+ Channels in Rat Sensory Neurons in Vitro and potent Peripheral Analgesis in Vivo", Molecular Pharmacology 66(5): 1223-1235, 2004.
Nakashima, et al., "The Anesthetic Steroid (+)-3alpha-Hydroxy-5alpha-androstane-17beta-carbonitrile Blocks N-, Q-, and R-Type, but not L- and P-Type, High Voltage Activated Ca2+ Current in Hippocampal and Dorsal Root Ganglion Neurons of the Rat", Molecular Pharmacology 54: 559-568, 1998.
Todorovic, et al., "Pharmacolog8ical properties of T-type CA2+ current in adult rat sensory neurons: effects of anticonvulsants and anesthetic agents", Journal of Neurophysiology 79: 240-252, 1998.
Olney, John W., et al., "Drug-induced Apoptotic Neurodegeneration in the Developing Brain", Symposium: Recent Mechanistic and Molecular Concepts in Neurotoxicology, Brain Pathology 2002; 12: 488-498.
Akk, Gustav, et al., "Neuroactive steroids have multiple actions to potentiate GABAA receptors", Journal Physiol 558.1. 2004, 59-74.
Alvarado et al., "Visual recognition memory is impaired in rhesus monkeys repeatedly exposed to sevoflurane in infancy," Br J Anaesth, 2017, 119, pp. 517-523, Published by Elsevier, Amsterdam.
Brambrink et al., "Isoflurane-induced apoptosis of oligodendrocytes in the neonatal primate brain," Ann Neurol, 2012, 72, pp. 525-535, Published by John Wiley & Sons, United States.
Brambrink et al., "Isoflurane-induced neuroapoptosis in the neonatal rhesus macaque brain," Anesthesiology, 2010, 112, pp. 834-841, Published by Lippincott Williams and Wilkins, United States.
Coleman et al., "Isoflurane Anesthesia Has Long-term Consequences on Motor and Behavioral Development in Infant Rhesus Macaques," Anesthesiology, 2017, 126, pp. 74-84, Published by Lippincott Williams and Wilkins, United States.
Creeley et al., Isoflurane-induced apoptosis of neurons and oligodendrocytes in the fetal rhesus macaque brain, Anesthesiology, 2014, 120, pp. 626-638, Published by Lippincott Williams and Wilkins, United States.
Creeley et al., "Propofol-induced apoptosis of neurones and oligodendrocytes in fetal and neonatal rhesus macaque brain," Br J Anaesth, 2013, 110, Suppl 1, pp. i29-838, Published by Elsevier, Amsterdam.

(Continued)

*Primary Examiner* — Nizal S Chandrakumar
(74) *Attorney, Agent, or Firm* — Rodney L. Sparks

(57) ABSTRACT

The present application discloses the unexpected result that a neuroactive steroid such as B260 can act as a general anesthetic and that it has no neurotoxic side effects such as impairing brain development.

10 Claims, 17 Drawing Sheets

(56) References Cited

OTHER PUBLICATIONS

Jevtovic-Todorovic et al., "Early exposure to common anesthetic agents causes widespread neurodegeneration in the developing rat brain and persistent learning deficits," J Neurosci, 2003, 23, 3, pp. 876-882, Published by the Society for Neuroscience, United States.

Jevtovic-Todorovic, "Exposure of developing brain to general anestheisa: What is the animal evidence?," Anesthesiology, 2018, 128, 4, pp. 832-839, Published by Lippincott Williams and Wilkins, United States.

Jevtovic-Todorovic, "Monkey business: the importance of mounting behavioural evidence for anaesthesia-Induced developmental neurotoxicity," 2018, Br J Anaesth, 120, 4, pp. 617-619, Published by Elsevier, Amsterdam.

Liu et al., "Potential Adverse Effects of Prolonged Sevoflurane Exposure on Developing Monkey Brain: From Abnormal Lipid Metabolism to Neuronal Damage," Toxicol. Sci, 2015, 147, pp. 562-572, Published by Oxford University Press, UK.

Noguchi et al., "Isoflurane exposure for three hours triggers apoptotic cell death in neonatal macaque brain," Br J Anaesth, 2017, 119, pp. 524-531, Published by Elsevier, Amsterdam.

Paule et al., "Ketamine anesthesia during the first week of life can cause long-lasting cognitive deficits in rhesus monkeys," Neurotoxicol Teratol, 2011, 33, pp. 220-230, Published by Elsevier, Amsterdam.

Raper et al., "Multiple anesthetic exposure to sevoflurane in infant monkeys alters emotional reactivity to an acute stressor," Anesthesiology, 2015, 123, pp. 1084-1092, Published by Lippincott Williams and Wilkins, United States.

Schenning et al., "Isoflurane exposure leads to apoptosis of neurons and oligodendrocytes in 20- and 40-day old rhesus macaques," Neurotoxicol Teratol, 2016, pii: S0892-0362: 30141-6, Published by Elsevier, Amsterdam.

Vlisides et al., "Neurotoxicity of General Anesthetics: An Update", Current Pharmaceutical Design, 2012, 18, pp. 6232-6240, Published by Bentham Science Publishers, Emirate of Sharjah, United Arab Emirates.

Wilder et al., "Early exposure to anesthesia and learning disabilities in a population-based cohort," Anesthesiology, 2009, 110, 4, pp. 796-804, Published by Lippincott Williams and Wilkins, United States.

* cited by examiner

GENERAL ANESTHETICS THAT ARE NOT NEUROTOXIC

RELATED APPLICATIONS

The present application is a national stage filing of International Application No. PCT/US2015/023320, filed Mar. 30, 2015, which claims priority under 35 U.S.C. § 119(e) from U.S. Provisional Application Ser. No. 61/971,589, filed Mar. 28, 2014, the disclosures of which are hereby incorporated by reference herein in their entirety.

STATEMENT REGARDING FEDERALLY SPONSORED RESEARCH OR DEVELOPMENT

This invention was made with government support under Grant Nos. HD044517 and GM070728, awarded by The National Institutes of Health. The government has certain rights in the invention.

BACKGROUND

Recently available scientific evidence presented over the last decade strongly suggests that early exposure to commonly used general anesthetics during critical periods of brain development results in undue death of the immature nerve cells and long-term impairments in behavior (Jevtovic-Todorovic et al., 2003). In addition to very strong animal evidence, rapidly emerging human evidence points at the link between exposure to general anesthesia during critical periods of brain development and learning disabilities later in life (Wilder et al., 2009).

All currently approved general anesthetics that are commonly used in daily pediatric practice have been shown to be neurotoxic and detrimental to cognitive development. Since general exposure is often a necessity that cannot be avoided when child's health is in danger it is imperative that we consider the development of novel anesthetics that are safe and effective in providing amnesia, lack of consciousness and insensitivity to pain while lacking neurotoxic effects described with the use of current general anesthetics.

It appears that general anesthetics commonly used to achieve complete general anesthesia state are potent modulators of two key neurotransmitters—a major excitatory neurotransmitter, glutamate [via blocking N-methyl-D aspartate (NMDA) receptors], and a major inhibitory neurotransmitter, γ-amino-butyric acid (via potentiating GABAA receptors). Since glutamate and GABA regulate all aspects of early brain development it comes as no surprise that brain development is negatively impacted when general anesthesia is employed. This realization is posing an interesting challenge—could novel anesthetic drugs be developed with the mechanism of anesthetic action that do not directly implicate either GABA of glutamate but rather modulate different receptor system, and once developed, whether novel anesthetics with different anesthetic target would prove to be as effective as the existing anesthetics but safe for very young individuals?

T-type channels were first described in sensory neurons of the dorsal root ganglion and were shown to activate with small membrane depolarizations, thus making them an important regulator of nociceptive sensory neuron excitability (Nelson et al., 2005). Recent evidence suggests that modulation of peripheral T-channels influences somatic (e.g. thermal and mechanical) and visceral nociceptive inputs and that inhibition of T-currents results in significant anti-nociception in a variety of animal pain models (Todorovic and Jevtovic-Todorovic, 2013). Importantly, B260 (also referred to as 3β-OH) shows strong analgesic properties in vivo (Todorovic et al., 2004). In addition to having great analgesic potentials, modulation of T-channels in thalamic neurons in the brain is hypothesized to promote sedation and sleep depending on the degree of T channel inhibition. In addition, we have demonstrated recently that inhibition of R-type calcium channels in the thalamus is important for hypnotic effects of general anesthetics (Joksovic et al., 2009).

There is a long felt need in the art for anesthetics that are not neurotoxic. The present invention satisfies this need.

SUMMARY OF THE INVENTION

We have addressed the issues described above by examining the class of agents that modulate neuronal activity via the inhibition of low voltage gated calcium ion channels called T-type channels (T-channels), as well as R-type high-voltage-activated calcium channels. Thus, the present strategy focused on developing novel anesthetics that are both T-channel and R-channel inhibitors as an approach for achieving effective and safe analgesia and general anesthesia.

The present application discloses the unexpected result that neuroactive steroid analgesics such as (3β, 5β, 17β)-3-hydroxyandrostane-17-carbonitrile (also referred to as B260, 3β5β-CN, or 3β-OH; see FIG. 1), act as a general anesthetic and, furthermore, that it is not neurotoxic compared to general anesthetics presently in use clinically. Therefore, the present invention provides for the use of 3β-OH (B260) as a non-neurotoxic anesthetic. It is also disclosed herein that a neuroactive steroid with anesthetic activity can induce potent spinally-mediated analgesia in a surgical incision model. It is also disclosed herein that it does not effect brain development, including early brain development, and that it is safe for non-adults, including very young subjects such as children. In one aspect, a child is an infant. The present invention further encompasses the use of other neuroactive steroids to practice the invention. Therefore, a neuroactive steroid of the invention is useful in pediatric anesthesia.

The present invention further provides for the use of a neuroactive steroid of the invention in adult subjects. In one aspect, an adult subject is an elderly subject. The lack of side effects of the compounds of the invention are useful for the elderly because the elderly are very sensitive to neurotoxic effects of currently use general anesthetics. Each of the indications provided herein, including, for example, use perioperative and post-operative, are included when referring to adult subjects.

In one embodiment, the anesthetics of the invention are neuroactive steroids. As disclosed herein, the neuroactive steroids compounds of the invention have a number of characteristics not shared with general anesthetic compounds used clinically today and do not have some of the same side effects that the general anesthetics have. Although many of the currently available neuroactive steroids are potentiators of $GABA_A$ receptors, the new class of agents that are of interest for this study are selective and potent T-channel blockers with a complete lack of glutamatergic or GABAergic properties. In one aspect, a neuroactive steroid analgesic has reduced neurotoxicity compared to a general anesthetic. In one aspect, a neuroactive steroid analgesic of the invention inhibits low voltage activated T-channel activity. In one aspect, the low voltage activated T-channel is Cav3.2. In one aspect, it inhibits low voltage activated R-channel activity. In one aspect, the low voltage activated R-channel is Cav2.3. In one aspect, the compounds of the invention are inhibitors of neuronal $Ca_v3.2$ (T-type calcium channel) and $Ca_v2.3$ (R-type calcium channel) currents in pain pathways. In one aspect, a compound of the invention inhibits the ability to feel pain and partially or completely reduces loss of sensation. In one aspect, it does not cause long-term impairments in synaptic neurotransmission. In one aspect, it does not cause long-term impairments in behavioral development. In one aspect, it reduces the risk in pediatric subjects of long-term behavioral impairment and impaired cognitive development compared to the long-term behavioral impairment and impaired cognitive development resulting from use of a neurotoxic general anesthetic. In one aspect, it has reduced neurotoxicity activity relative to other anesthetics. In one aspect, it has no significant blocking effect on GABAA-mediated current, NMDA-mediated current, voltage-gated Na+ current, voltage-gated and K+ current, N-type Ca2+ current, or L-type Ca2+ current. In one embodiment, a neuroactive steroid analgesic of the invention has at least two or all of the characteristics summarized in this paragraph.

Useful neuroactive steroids of the invention include the following, as well as active analogs and derivatives thereof:
3β-OH (also referred to as B260 and 3β,5β-CN)—(3β, 5β,17β)-3-hydroxyandrostane-17-carbonitrile;
Alphaxalone—(3α,5α)3-hydroxypregnane-11,20-dione;
ACN—(3α,5α,17β)-3-hydroxyandrostane-17-carbonitrile;
CDNC24—(3α,5α)-3-hydroxy-13,24-cyclo-18,21-dinorchol-22-en-24-ol; and
ECN—(3β,5α,17β)-17-hydroxyestrane-3-carbonitrile.
These compounds have the following structures:

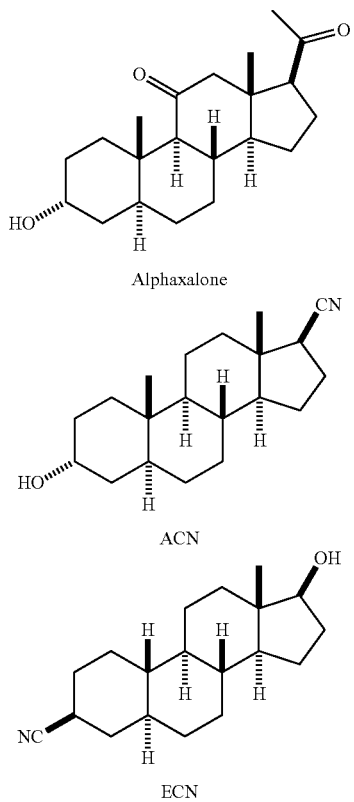

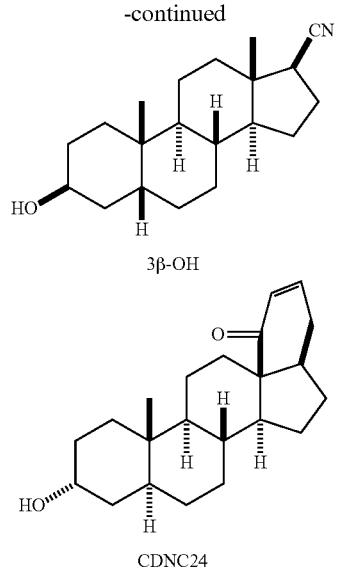

In one aspect, an anesthetic of the invention is administered intravenously. In one aspect, it can be introduced into the cerebrospinal fluid. In one aspect, it can be introduced intrathecally. In one aspect, it can be administered epidurally. In one aspect, an anesthetic of the invention can be administered as an aerosol. In one aspect, it can be inhaled. In one aspect, it can be administered intracisternally. One of ordinary skill in the art will appreciate that various routes of administration can be used and that doses may vary depending on factors such as the age, weight, sex, and health of the subject. In one aspect, an anesthetic of the invention is a 5β-reduced steroid. In one aspect, the 5β-reduced steroid is (3β, 5β, 17β)-3-hydroxyandrostane-17-carbonitrile, also known as B260, 3β-OH and 3β5β-CN. In one aspect, a dose of a compound of the invention can range from about 0.1 mg/kg to about 100 mg/kg. In another aspect, it can range from about 1.0 mg/kg to about 50 mg/kg. In another aspect, it can range from about 5.0 mg/kg to about 75 mg/kg. In yet another aspect, a dose can range from about 5.0 mg/kg to about 25 mg/kg. For example, a dose could be about 0.1, 0.5, 1.0, 2.0, 3.0, 4.0, 5.0, 6.0, 7.0, 8.0, 9.0, 10.0, 11.0, 12.0, 13.0, 14.0, 15.0, 16.0, 17.0, 18.0, 19.0, 20.0, 25.0, 30.0, 35, 40, 45, 50, 60, 70, 80, 90, or 100 mg/kg. In one aspect, a unit dose can be administered. Depending on the dose given to a subject, it can also be administered more than once and when administered more than once the intervals can be varied and the dose and intervals can be determined by the physician, anesthesiologist, or nurse anesthetist in charge of anesthesia.

Unless indicated otherwise, a neuroactive steroid analgesic of the invention is not co-administered with a currently used general anesthetic or used in conjunction with another general anesthetic. However, the present invention does provide for combination uses of neuroactive steroid analgesics with other known general anesthetics.

In one embodiment, the compositions and methods of the invention are useful for pediatric anesthesia.

In one embodiment, a composition of the invention can be used to induce spinally-mediated anesthesia.

In one embodiment, the present invention provides compositions and methods for treating perioperative hyperalgesia.

In one embodiment, the present invention provides compositions and methods for treating postoperative pain.

In one embodiment, a subject of the invention is a pediatric subject. In one embodiment, the subject is an adult. In one aspect, the adult is an elderly adult.

In one embodiment, a compound of the invention does not cause long-term impairment of memory.

In one embodiment, a compound of the invention does not cause long-term impairment of learning. In one aspect, the learning is spatial learning.

In one embodiment, the neuroactive steroid analgesic induces analgesia.

In one embodiment, the neuroactive steroid analgesic is administered intravenously or by inhalation. One of ordinary skill in the art can determine the best route of administration.

In one aspect, the neuroactive steroid analgesic comprises hypnotic activity.

In one aspect, the neuroactive steroid analgesic of the invention inhibits perioperative pain.

In one aspect, the method of the invention inhibits postoperative pain. In one aspect, the pain is associated with a surgical wound.

In one aspect, the neuroactive steroid analgesic of the invention inhibits development of hyperalgesia.

In one embodiment, a neuroactive steroid of the invention inhibits hyperalgesia for at least 24 hours post-surgery. In one aspect, it inhibits hyperalgesia for about 24 hours after surgery. In one aspect, it inhibits hyperalgesia for at least 48 hours after surgery. In one aspect, it inhibits hyperalgesia for about 48 hours after surgery.

In one aspect, the neuroactive steroid analgesic of the invention inhibits development of thermal hyperalgesia.

In one embodiment, the method of the invention includes administering the neuroactive steroid analgesic to provide anesthesia for surgery for periods of between about 3 to 12 hours and analgesia after surgery for at least 48 hours. One of ordinary skill in the art can determine the dose, number of doses to be used, etc. to meet these criteria or can adjust them to vary the times.

One of ordinary skill in the art can determine the dose to be used depending on factors such as the procedure to be done, the age, sex, weight, and health of the subject, etc. In one aspect, a neuroactive steroid analgesic is administered at a dose ranging from about 1 mg/kg/body weight to about 200 mg/kg body weight. In another aspect, the dose ranges from about 2 mg/kg to about 100 mg/kg body weight. In one aspect, the dose ranges from about 3 mg/kg/body weight to about 75 mg/kg body weight. In another aspect, the dose ranges from about 5 mg/kg/body weight to about 25 mg/kg body weight. In one aspect, a unit dose can be administered.

In one embodiment, a compound of the invention is also an analgesic. In one aspect, a compound of the invention does not cause neuronal damage in the developing brain. In one aspect, use of a compound of the invention does not result in long-term learning impairments. In one aspect, use of a compound of the invention does not impair cognitive development.

In one aspect, a compound of the invention can be administered with another type of drug or agent, such a different type of anesthetic or with a therapeutic compound or antibiotic.

The present invention further provides pharmaceutical compositions comprising at least one neuroactive steroid analgesic of the invention, optionally a pharmaceutically-acceptable carrier, and optionally an additional therapeutic agent.

The present invention further provides a kit comprising at least one neuroactive steroid analgesic of the invention, optionally a pharmaceutically-acceptable carrier, optionally an additional therapeutic agent, an applicator, and an instructional material.

Various aspects and embodiments of the invention are described in further detail below.

DETAILED DESCRIPTION

Figure 1:
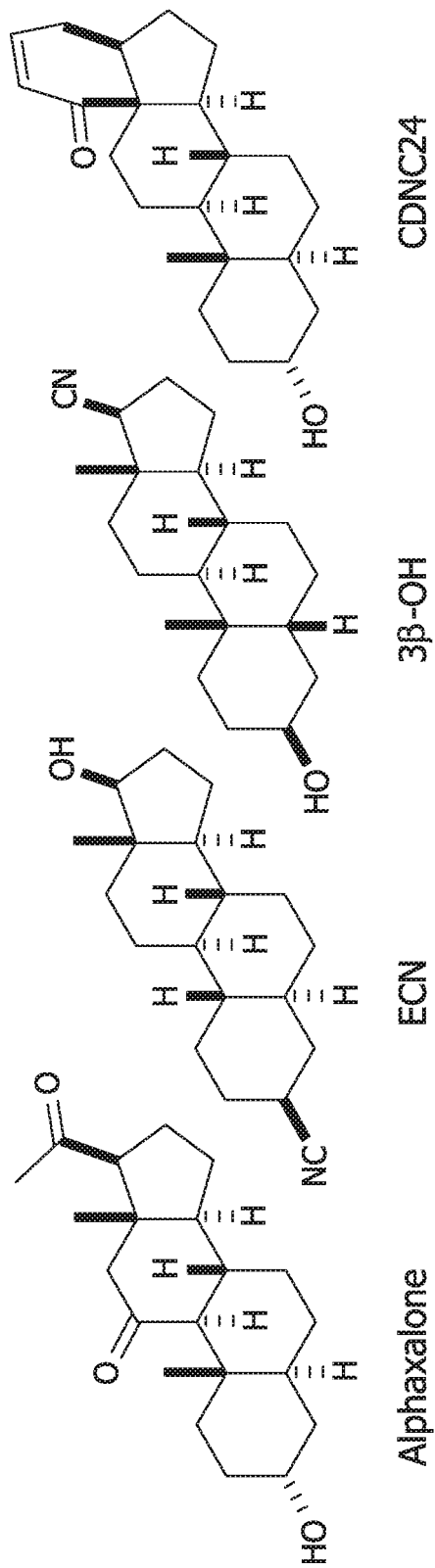
FIG. 1. Structures of neuroactive steroids used in previous studies.

Abbreviations and Acronyms
3β5β-CN—(3β,5β,17β)-3-hydroxyandrostane-17-carbonitrile, also referred to as B260 and 3β-OH herein 3β-OH—(3β,5β,17β)-3-hydroxyandrostane-17-carbonitrile, also referred to as B260 and 3β5β-CN herein
ACN—(3α,5α,17β)-3-hydroxyandrostane-17-carbonitrile
ADP—after depolarizing potential
Alphaxalone—(3α,5α)3-hydroxypregnane-11,20-dione
AP—action potential
B260—(3β, 5β, 17β)-3-hydroxyandrostane-17-carbonitrile; also referred to as 3β-OH and 3β5β-CN herein.
CDNC24—(3α,5α)-3-hydroxy-13,24-cyclo-18,21-dinorchol-22-en-24-ol
CYCL—cyclodextrin
DH—dorsal horn
DRG—dorsal root ganglion
ECN—(3β,5α,17β)-17-hydroxyestrane-3-carbonitrile
$ED_{50}$—dose that produces 50% effect
GA—general anesthetic
GABA—γ-amino-butyric acid
HVA—high voltage activated
i.p.—intraperitoneally
i.pl.—intraplantar
i.t.—intrathecal
KET—ketamine
$LD_{50}$—lethal dose for 50% of animals
LORR—loss of righting reflex
LTP—long term potentiation
LVA—low voltage activated
NMDA—N-Methyl-D Aspartate
PND—postnatal day
PWL—paw withdrawal latency
$R_{in}$—input resistance
RMP—resting membrane potential
SAL—saline
VGCC—voltage gated calcium channel Definitions In describing and claiming the invention, the following terminology will be used in accordance with the definitions set forth below. Unless defined otherwise, all technical and scientific terms used herein have the commonly understood by one of ordinary skill in the art to which the invention pertains. Although any methods and materials similar or equivalent to those described herein may be useful in the practice or testing of the present invention, preferred methods and materials are described below. Specific terminology of particular importance to the description of the present invention is defined below.

The articles "a" and "an" are used herein to refer to one or to more than one (i.e., to at least one) of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 20% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

The terms "additional therapeutically active compound" or "additional therapeutic agent", as used in the context of the present invention, refers to the use or administration of a compound for an additional therapeutic use for a particular injury, disease, or disorder being treated. Such a compound, for example, could include one being used to treat an unrelated disease or disorder, or a disease or disorder which may not be responsive to the primary treatment for the injury, disease or disorder being treated.

As use herein, the terms "administration of" and or "administering" a compound should be understood to mean providing a compound of the invention or a prodrug of a compound of the invention to a subject in need of treatment.

As used herein, the term "aerosol" refers to suspension in the air. In particular, aerosol refers to the particlization or atomization of a formulation of the invention and its suspension in the air.

As used herein, an "agonist" is a composition of matter which, when administered to a mammal such as a human, enhances or extends a biological activity attributable to the level or presence of a target compound or molecule of interest in the mammal.

The term "allodynia", as used herein, refers to a condition in which ordinarily nonpainful stimuli evoke pain.

The term "analgesia", as used herein, refers to absence of sensibility to pain, particularly the relief of pain without loss of consciousness; absence of pain or noxious stimulation.

As used herein, an "analog", or "analogue" of a chemical compound is a compound that, by way of example, resembles another in structure but is not necessarily an isomer (e.g., 5-fluorouracil is an analog of thymine).

As used herein, "anesthesia" refers to loss of the ability to feel pain and a partial or complete loss of sensation, caused by administration of a drug or other medical intervention and is a local or general insensibility to pain with or without the loss of consciousness. "Epidural anesthesia" refers to that produced by injection of the anesthetic into the extradural space, either between the vertebral spines or into the sacral hiatus (caudal block). "General anesthesia" refers to a state of unconsciousness and insusceptibility to pain, produced by administration of anesthetic agents by, for example, inhalation, intravenously, intramuscularly, rectally, or via the gastrointestinal tract. "Spinal anesthesia" refers to a regional anesthesia by injection of a local anesthetic into the subarachnoid space around the spinal cord.

The term "anesthetic", as used herein, refers to a drug or agent capable of producing a complete or partial loss of feeling (anesthesia).

An "antagonist" is a composition of matter which when administered to a mammal such as a human, inhibits a biological activity attributable to the level or presence of a compound or molecule of interest in the mammal.

The term "antimicrobial agents" as used herein refers to any naturally-occurring, synthetic, or semi-synthetic compound or composition or mixture thereof, which is safe for human or animal use as practiced in the methods of this invention, and is effective in killing or substantially inhibiting the growth of microbes. "Antimicrobial" as used herein, includes antibacterial, antifungal, and antiviral agents.

The term "biocompatible", as used herein, refers to a material that does not elicit a substantial detrimental response in the host.

As used herein, the term "chemically conjugated," or "conjugating chemically" refers to linking the antigen to the carrier molecule. This linking can occur on the genetic level using recombinant technology, wherein a hybrid protein may be produced containing the amino acid sequences, or portions thereof, of both the antigen and the carrier molecule. This hybrid protein is produced by an oligonucleotide sequence encoding both the antigen and the carrier molecule, or portions thereof. This linking also includes covalent bonds created between the antigen and the carrier protein using other chemical reactions, such as, but not limited to glutaraldehyde reactions. Covalent bonds may also be created using a third molecule bridging the antigen to the carrier molecule. These cross-linkers are able to react with groups, such as but not limited to, primary amines, sulfhydryls, carbonyls, carbohydrates, or carboxylic acids, on the antigen and the carrier molecule. Chemical conjugation also includes non-covalent linkage between the antigen and the carrier molecule.

A "compound," as used herein, refers to any type of substance or agent that is commonly considered a drug, or a candidate for use as a drug, as well as combinations and mixtures of the above.

A "control" cell is a cell having the same cell type as a test cell. The control cell may, for example, be examined at precisely or nearly the same time the test cell is examined. The control cell may also, for example, be examined at a time distant from the time at which the test cell is examined, and the results of the examination of the control cell may be recorded so that the recorded results may be compared with results obtained by examination of a test cell.

A "test" cell is a cell being examined.

As used herein, a "derivative" of a compound refers to a chemical compound that may be produced from another compound of similar structure in one or more steps, as in replacement of H by an alkyl, acyl, or amino group.

The use of the word "detect" and its grammatical variants refers to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, an "effective amount" or "therapeutically effective amount" means an amount sufficient to produce a selected effect, such as alleviating symptoms of a disease or disorder. In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amounts of each compound may vary. The term "more effective" means that the selected effect is alleviated to a greater extent by one treatment relative to the second treatment to which it is being compared.

The term "elixir," as used herein, refers in general to a clear, sweetened, alcohol-containing, usually hydroalcoholic liquid containing flavoring substances and sometimes active medicinal agents.

As used in the specification and the appended claims, the terms "for example," "for instance," "such as," "including" and the like are meant to introduce examples that further clarify more general subject matter. Unless otherwise specified, these examples are provided only as an aid for understanding the invention, and are not meant to be limiting in any fashion.

The terms "formula" and "structure" are used interchangeably herein.

As used herein, a "functional" biological molecule is a biological molecule in a form in which it exhibits a property by which it is characterized. A functional enzyme, for example, is one that exhibits the characteristic catalytic activity by which the enzyme is characterized.

The term "general anesthetic" as used herein when referring to anesthetics, means those in use prior to the present invention and includes clinically used general anesthetics such as ketamine, nitrous oxide, isoflurane, propofol, and etomidate.

As used herein, "homology" is used synonymously with "identity."

The term "hyperalgesia", as used herein, refers to an extreme or increased sensitivity to pain.

As used herein, the term "inhaler" refers both to devices for nasal and pulmonary administration of a drug, e.g., in solution, powder and the like. For example, the term "inhaler" is intended to encompass a propellant driven inhaler, such as is used to administer antihistamine for acute asthma attacks, and plastic spray bottles, such as are used to administer decongestants.

The term "inhibit," as used herein, refers to the ability of a compound, agent, or method to reduce or impede a described function, level, activity, rate, etc., based on the context in which the term "inhibit" is used. Preferably, inhibition is by at least 10%, more preferably by at least 25%, even more preferably by at least 50%, and most preferably, the function is inhibited by at least 75%. The term "inhibit" is used interchangeably with "reduce" and "block."

The term "inhibit a complex," as used herein, refers to inhibiting the formation of a complex or interaction of two or more proteins, as well as inhibiting the function or activity of the complex. The term also encompasses disrupting a formed complex. However, the term does not imply that each and every one of these functions must be inhibited at the same time.

As used herein "injecting or applying" includes administration of a compound of the invention by any number of routes and means including, but not limited to, topical, oral, buccal, intravenous, intramuscular, intra arterial, intramedullary, intrathecal, intraventricular, transdermal, subcutaneous, intraperitoneal, intranasal, enteral, topical, sublingual, vaginal, ophthalmic, pulmonary, or rectal means.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

A "ligand" is a compound that specifically binds to a target receptor.

A "receptor" is a compound that specifically binds to a ligand.

A ligand or a receptor (e.g., an antibody) "specifically binds to" or "is specifically immunoreactive with" a compound when the ligand or receptor functions in a binding reaction which is determinative of the presence of the compound in a sample of heterogeneous compounds.

As used herein, the term "linkage" refers to a connection between two groups.

The connection can be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, e.g., through ionic or hydrogen bonds or van der Waals interactions, e.g., a nucleic acid molecule that hybridizes to one complementary sequence at the 5' end and to another complementary sequence at the 3' end, thus joining two non-complementary sequences.

The term "modulate", as used herein, refers to changing the level of an activity, function, or process. The term "modulate" encompasses both inhibiting and stimulating an activity, function, or process.

The term "neurotoxic general anesthetic", as used herein, refers to one that has neurotoxic effects when used on children.

The term "not neurotoxic" or "non-neurotoxic" as used herein means that a compound has reduced neurotoxicity compared with general anesthetics used today. Reduced means at least by 5% for one of the categories described herein. For example, one of the useful compounds of the invention, 3β-OH, has now been found to be an effective anesthetic, particularly in young animals where it has very reduced side effects on cognitive development, long-term behavioral impairment, impairment of learning, etc. compared with the effects of general anesthetics in use today.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

As used herein, the term "perioperative" generally refers to the three phases of surgery: preoperative, intraoperative, and postoperative.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

As used herein, the term "pharmaceutically-acceptable carrier" means a chemical composition with which an appropriate compound or derivative can be combined and which, following the combination, can be used to administer the appropriate compound to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

"Pharmaceutically acceptable" means physiologically tolerable, for either human or veterinary application.

As used herein, "pharmaceutical compositions" include formulations for human and veterinary use.

"Plurality" means at least two.

The term "prevent," as used herein, means to stop something from happening, or taking advance measures against something possible or probable from happening. In the context of medicine, "prevention" generally refers to action taken to decrease the chance of getting a disease or condition.

A "preventive" or "prophylactic" treatment is a treatment administered to a subject who does not exhibit signs, or exhibits only early signs, of a disease or disorder. A prophylactic or preventative treatment is administered for the purpose of decreasing the risk of developing pathology associated with developing the disease or disorder.

A "prophylactic" treatment is a treatment administered to a subject who does not exhibit signs of a disease or exhibits only early signs of the disease for the purpose of decreasing the risk of developing pathology associated with the disease.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug, or may demonstrate increased palatability or be easier to formulate.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure. In particular, purified sperm cell DNA refers to DNA that does not produce significant detectable levels of non-sperm cell DNA upon PCR amplification of the purified sperm cell DNA and subsequent analysis of that amplified DNA. A "significant detectable level" is an amount of contaminate that would be visible in the presented data and would need to be addressed/explained during analysis of the forensic evidence.

A "receptor" is a compound that specifically binds to a ligand.

A "ligand" is a compound that specifically binds to a target receptor.

The term "regulate" refers to either stimulating or inhibiting a function or activity of interest.

A "sample," as used herein, refers preferably to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest. A sample can also be obtained from cell or tissue culture.

By the term "specifically binds to", as used herein, is meant when a compound or ligand functions in a binding reaction or assay conditions which is determinative of the presence of the compound in a sample of heterogeneous compounds.

The term "standard," as used herein, refers to something used for comparison. For example, it can be a known standard agent or compound which is administered and used for comparing results when administering a test compound, or it can be a standard parameter or function which is measured to obtain a control value when measuring an effect of an agent or compound on a parameter or function. Standard can also refer to an "internal standard", such as an agent or compound which is added at known amounts to a sample and is useful in determining such things as purification or recovery rates when a sample is processed or subjected to purification or extraction procedures before a marker of interest is measured. Internal standards are often a purified marker of interest which has been labeled, such as with a radioactive isotope, allowing it to be distinguished from an endogenous marker.

A "subject" of analysis, diagnosis, or treatment is an animal. Such animals include mammals, preferably a human.

As used herein, a "subject in need thereof" is a patient, animal, mammal, or human, who will benefit from the method of this invention.

The term "symptom," as used herein, refers to any morbid phenomenon or departure from the normal in structure, function, or sensation, experienced by the patient and indicative of disease. In contrast, a "sign" is objective evidence of disease. For example, a bloody nose is a sign. It is evident to the patient, doctor, nurse and other observers.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

The term to "treat," as used herein, means reducing the frequency with which symptoms are experienced by a patient or subject or administering an agent or compound to reduce the frequency with which symptoms are experienced.

As used herein, the term "treating" includes prophylaxis of the specific disorder or condition, or alleviation of the symptoms associated with a specific disorder or condition and/or preventing or eliminating said symptoms.

A "prophylactic" treatment is a treatment administered to a subject who does not exhibit signs of a disease or exhibits only early signs of the disease for the purpose of decreasing the risk of developing pathology associated with the disease.

Chemical Definitions

As used herein, the term "halogen" or "halo" includes bromo, chloro, fluoro, and iodo.

The term "haloalkyl" as used herein refers to an alkyl radical bearing at least one halogen substituent, for example, chloromethyl, fluoroethyl or trifluoromethyl and the like.

The term "$C_1$-$C_n$ alkyl" wherein n is an integer, as used herein, represents a branched or linear alkyl group having from one to the specified number of carbon atoms. Typically, $C_1$-$C_6$ alkyl groups include, but are not limited to, methyl, ethyl, n-propyl, iso-propyl, butyl, iso-butyl, sec-butyl, tert-butyl, pentyl, hexyl, and the like.

The term "$C_2$-$C_n$ alkenyl" wherein n is an integer, as used herein, represents an olefinically unsaturated branched or linear group having from 2 to the specified number of carbon atoms and at least one double bond. Examples of such groups include, but are not limited to, 1-propenyl, 2-propenyl, 1,3-butadienyl, 1-butenyl, hexenyl, pentenyl, and the like.

The term "$C_2$-$C_n$ alkynyl" wherein n is an integer refers to an unsaturated branched or linear group having from 2 to the specified number of carbon atoms and at least one triple bond. Examples of such groups include, but are not limited to, 1-propynyl, 2-propynyl, 1-butynyl, 2-butynyl, 1-pentynyl, and the like.

The term "$C_3$-$C_n$ cycloalkyl" wherein n=8, represents cyclopropyl, cyclobutyl, cyclopentyl, cyclohexyl, cycloheptyl, and cyclooctyl.

As used herein, the term "optionally substituted" typically refers to from zero to four substituents, wherein the substituents are each independently selected. Each of the independently selected substituents may be the same or different than other substituents. For example, the substituents of an R group of a formula may be optionally substituted (e.g., from 1 to 4 times) with independently selected H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain and amino acid.

As used herein the term "aryl" refers to an optionally substituted mono- or bicyclic carbocyclic ring system having one or two aromatic rings including, but not limited to, phenyl, benzyl, naphthyl, tetrahydronaphthyl, indanyl, indenyl, and the like. A Optionally substituted aryl@ includes aryl compounds having from zero to four substituents, and A substituted aryl@ includes aryl compounds having one or more substituents. The term ($C_5$-$C_8$ alkyl)aryl refers to any aryl group which is attached to the parent moiety via the alkyl group.

"Heterocycle" refers to any stable 4, 5, 6, 7, 8, 9, 10, 11, or 12 membered, (unless the number of members is otherwise recited), monocyclic, bicyclic, or tricyclic heterocyclic ring that is saturated or partially unsaturated, and which consists of carbon atoms and 1, 2, 3, or 4 heteroatoms independently selected from the group consisting of N, O, and S. If the heterocycle is defined by the number of carbons atoms, then from 1, 2, 3, or 4 of the listed carbon atoms are replaced by a heteroatom. If the heterocycle is bicyclic or tricyclic, then at least one of the two or three rings must contain a heteroatom, though both or all three may each contain one or more heteroatoms. The N group may be N, NH, or N-substituent, depending on the chosen ring and if substituents are recited. The nitrogen and sulfur heteroatoms optionally may be oxidized (e.g., S, S(O), S(O)$_2$, and N—O). The heterocycle may be attached to its pendant group at any heteroatom or carbon atom that results in a stable structure. The heterocycles described herein may be substituted on carbon or on a nitrogen atom if the resulting compound is stable.

"Heteroaryl" refers to any stable 5, 6, 7, 8, 9, 10, 11, or 12 membered, (unless the number of members is otherwise recited), monocyclic, bicyclic, or tricyclic heterocyclic ring that is aromatic, and which consists of carbon atoms and 1, 2, 3, or 4 heteroatoms independently selected from the group consisting of N, O, and S. If the heteroaryl is defined by the number of carbons atoms, then 1, 2, 3, or 4 of the listed carbon atoms are replaced by a heteroatom. If the heteroaryl group is bicyclic or tricyclic, then at least one of the two or three rings must contain a heteroatom, though both or all three may each contain one or more heteroatoms. If the heteroaryl group is bicyclic or tricyclic, then only one of the rings must be aromatic. The N group may be N, NH, or N-substituent, depending on the chosen ring and if substituents are recited. The nitrogen and sulfur heteroatoms may optionally be oxidized (e.g., S, S(O), S(O)$_2$, and N—O). The heteroaryl ring may be attached to its pendant group at any heteroatom or carbon atom that results in a stable structure. The heteroaryl rings described herein may be substituted on carbon or on a nitrogen atom if the resulting compound is stable."

The term "heteroatom" means for example oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring.

The term "bicyclic" represents either an unsaturated or saturated stable 7- to 12-membered bridged or fused bicyclic carbon ring. The bicyclic ring may be attached at any carbon atom which affords a stable structure. The term includes, but is not limited to, naphthyl, dicyclohexyl, dicyclohexenyl, and the like.

The compounds of the present invention contain one or more asymmetric centers in the molecule. In accordance with the present invention a structure that does not designate the stereochemistry is to be understood as embracing all the various optical isomers, as well as racemic mixtures thereof.

The compounds of the present invention may exist in tautomeric forms and the invention includes both mixtures and separate individual tautomers. For example the following structure:

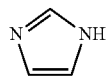

is understood to represent a mixture of the structures:

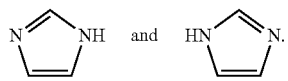

The term "pharmaceutically-acceptable salt" refers to salts which retain the biological effectiveness and properties of the compounds of the present invention and which are not biologically or otherwise undesirable. In many cases, the compounds of the present invention are capable of forming acid and/or base salts by virtue of the presence of amino and/or carboxyl groups or groups similar thereto.

Compounds of the present invention that have one or more asymmetric carbon atoms may exist as the optically pure enantiomers, or optically pure diastereomers, as well as mixtures of enantiomers, mixtures of diastereomers, and racemic mixtures of such stereoisomers. The present invention includes within its scope all such isomers and mixtures thereof.

Embodiments

Over the last decade animal data and rapidly emerging clinical evidence strongly suggest that exposure to anesthetics and sedatives during critical stages of brain development (often referred to as synaptogenesis) results in long-lasting (perhaps permanent) impairment in cognitive and behavioral development. These new findings are likely to have a lasting impact on anesthesia and sedation practices in pediatrics. Because currently used general anesthetics (GAs) known to be neurotoxic to the immature brain exert their action by modulating two main receptor systems—GABA and NMDA—it is hypothesized herein that novel anesthetics with different mechanisms of action might be safe and promising alternatives. One such alternative is a family of neuroactive steroid analogs (e.g. B260) with selective blocking action on voltage-gated calcium channels (VGCCs), specifically low-voltage-activated T-type (CaV3.2) and R-type (CaV2.3) channels known to play a crucial role in neuronal excitability and synaptic transmission. Data disclosed herein show that these analgesic T-channel-blocking neuroactive steroids can also can be effective hypnotics. Most importantly, compared with other injectable (and inhaled) GAs, B260 appear to be much less harmful to the developing brain. The ultimate innovation and, importantly, clinical value of this patent lies in the potential to design a greatly improved anesthetic that would be safe and effective for use in pediatric anesthesia.

Furthermore, most commonly GAs do not provide a level of analgesia that is required for surgical procedures, necessitating the use of other agents such as opioid analgesics in the perioperative period. Although opioids are very effective in treating the acute pain associated with surgical procedures, they are only partially effective for more chronic painful disorders, and their use is associated with side effects including constipation, urinary retention, impaired cognitive function, respiratory depression, tolerance and addiction. It is disclosed herein that neuroactive steroids with anesthetic capacity such as B260 induce potent spinally-mediated analgesia in an animal model of surgical incision. Hence, B260 and related neuroactive steroids represent a new class of GAs with unique analgesic properties following systemic, intrathecal, and peripheral delivery. In addition to disclosing new general anesthetics that are not neurotoxic for the developing brain, it is also disclosed that these neuroactive steroids are useful as novel therapies for perioperative pain that may greatly decrease the need for narcotics and potential for drug abuse.

In one embodiment, a compound of the invention (referred to as either 3β-OH or B260) has the structure:

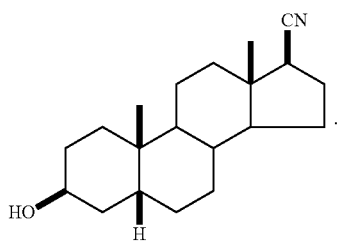 [SMILES: C[C@]12CCC3C(CC[C@@H]4C[C@@H](O)CC[C@]34C)C1CC[C@@H]2C#N]

The invention further includes biologically active derivatives and analogs of the compound provided above. The compound can be prepared as described in Han et al. (J. Med. Chem., 1996, 39 (21), pp 4218-4232). See also, Paradiso et al. (Molecular Pharmacology Aug. 1, 2000, vol. 58, no. 2, 341-351).

Useful compounds of the invention include, but are not limited to, alphaxalone [(3α,5α)3-hydroxypregnane-11,20-dione] and a related compound, ACN [(3α,5α,17β)-3-hydroxyandrostane-17-carbonitrile], both steroid anesthetics that are potent GABAergic agents (Todorovic et al., 1998; Pathirathna et al., 2005a), ECN [(3β,5α,17β)-17-hydroxyestrane-3-carbonitrile] (Todorovic et al., 1998), ACN's stereoisomer, 3β-OH [(3β,5β,17β)-3-hydroxyandrostane-17-carbonitrile] (Joksovic et al., 2007; Wang et al., 2002; Todorovic et al., 2004b), and CDNC24 [(3α,5α)-3-hydroxy-13,24-cyclo-18,21-dinorchol-22-en-24-ol] (Pathirathna et al., 2005a).

In one embodiment, the present invention provides novel activity of neurosteroid anesthetics for use in perioperative analgesia. Most commonly used injectable general anesthetics (GAs) do not provide a level of analgesia that is required for surgical procedures, necessitating the use of other agents such as opioid analgesics in the perioperative period. Although opioids are very effective in treating the acute pain associated with surgical procedures, they are only partially effective for more chronic painful disorders, and their use is associated with side effects including constipation, urinary retention, impaired cognitive function, respiratory depression, tolerance and addiction. More than 12 million people in United States abused opioids in 2010 (Meyer et al., 2014), resulting in more overdose deaths than heroin and cocaine combined (National Center for Health Statistics, 2012). Other currently available medications have either limited efficacy or serious side effects. Thus, further research into new therapeutic modalities for treatment of pain in the perioperative period was warranted and results are disclosed herein.

In one embodiment, a neuroactive compound of the invention is useful for treatment of pain in the perioperative period.

In one embodiment, a neuroactive compound of the invention is useful for treatment of pain in the postoperative period.

Without wishing to be bound by any particular theory it is hypothesized herein that inhibition of neuronal $Ca_v3.2$ T-type calcium currents and $Ca_v2.3$ (R-subtype) of voltage-gated calcium currents in pain pathways underlies potent analgesia with a novel anesthetic 3β-OH and related neuroactive steroids. Calcium ($Ca^{2+}$) influx through appropriately localized voltage-gated calcium channels (VGCCs) channels is the major trigger for the release of synaptic vesicles from neuronal presynaptic terminals in response to noxious stimulation. An increase of intracellular $Ca^{2+}$ in pain sensing neurons (nociceptors) can also influence the excitability of these cells. Prior studies indicate that the blockade of $Ca_v3.2$ T-currents in nociceptive dorsal root ganglion (DRG) neurons by 5β-reduced steroids underlies their potent peripheral anti-nociceptive effects (Todorovic et al., 2004; Ayoola et al., 2014). It is disclosed herein that 3β-OH [(3β,5β,17β)-3-hydroxyandrostane-17-carbonitrile] in addition to hypnotic properties, also displays excellent spinally-mediated analgesia. We also found that 3β-OH inhibits recombinant $Ca_v2.3$ (R-type) HVA currents with a similar potency to that of DRG $Ca_v3.2$ T-current. Thus, 3β-OH and related steroid molecules may represent a novel class of GAs and VGCCs blockers having desirable and unique analgesic properties following systemic and intrathecal delivery, as well as delivery to the site of tissue injury.

The present application provides methods and techniques useful for making and identifying other useful compounds. The art provides other useful methods and techniques. For example, in vivo pain studies in rats and mice can establish dose-response relationships for 3β-OH and other related steroid molecules for their analgesic efficacy in a clinically-relevant rat model of skin and deep tissue incision. The steroid compounds can be injected directly into the site of tissue injury, intrathecally or systemically to establish analgesic dosing that does not affect sensory-motor performance. Methods are provided, or are known in the art, to study the mechanisms of steroid-induced analgesia using a pharmacological approach and by using knockout mice lacking specific VGCCs. Without wishing to be bound by any particular theory, it is hypothesized herein that peripheral analgesia of steroids is mediated via inhibition of $Ca_v3.2$ T-type channels, whereas spinal analgesia is synergistically mediated via inhibition of both $Ca_v2.3$ and $Ca_v3.2$ channels.

Further methods include the use of an acute spinal cord preparation to study the effects of 3β-OH and related steroid analogues on spontaneous and evoked synaptic currents, as well as spike firing in identified nociceptive projection neurons in spinal dorsal horn (DH), the main pain processing region in CNS. These studies will define the whole-cell neurophysiological effects of test compounds in the major nociceptive pathway. We will also use immunohistochemistry and electron microscopy to study cellular and subcellular localization of $Ca_v2.3$ and $Ca_v3.2$ channels in DH neurons.

Methods are disclosed herein or in the art to study mechanisms and structure-activity relationships of steroid inhibition of VGCCs to develop and test other neuroactive steroids for the properties described herein. The invention encompasses new molecules discovered or designed that are potent and selective inhibitors of $Ca_v3.2$ and $Ca_v2.3$ channels that are useful as safer anesthetics and analgesics. Furthermore, biophysical mechanisms of channel inhibition by 3β-OH and other lead compounds can be used. Lead compounds will be tested in ensuing in vivo studies using a rodent model of acute and chronic post-operative incisional pain.

Administration can be by various injection routes or types of administration, including, but not limited to, direct, topical, nasal, aerosol, i.v., intra-arterial, subarachnoid, epidural, intra-cisternal, i.t., and ip.

In one embodiment, a compound of the invention is useful to provide anesthesia for surgery for periods of between 3 and 12 hours, and analgesia after surgery for at least 24 hours.

The compositions and dosage forms of the invention are useful for the administration of anesthetics for a variety of therapeutic purposes and procedures. Thus, for example, the compositions may be prepared for administration as blocks in advance of various surgical procedures, and for the treatment or prevention of pain, whether in advance of a surgical procedure or in treatment of a pre-existing condition; and more generally, for pain management, e.g. as part of a treatment regimen.

In one embodiment, the invention provides compositions and methods for providing anesthesia to a subject having a wound, such as a laceration, a surgical incision, an ulcer, an abrasion or a burn, the method comprising the step of applying topically to the wound a composition of the invention.

As described herein, the compositions of the present invention comprise, as an active agent, at least one compound having the structure of, or is an analog or derivative of any of the formulas or compounds disclosed herein. If desired, the compositions may further comprise one or more additional active agents. Where it is appropriate, any of the active agents may be administered in the form of the compound per se, and/or in the form of a salt, polymorph, ester, amide, prodrug, derivative, or the like, provided the salt, polymorph, ester, amide, prodrug or derivative is suitable pharmacologically. Where it is appropriate, salts, esters, amides, prodrugs and other derivatives of the active agents may be prepared using standard procedures known to those skilled in the art of synthetic organic chemistry and described, for example, by J. March, Advanced Organic Chemistry: Reactions, Mechanisms and Structure, 4th Ed. (New York: Wiley-Interscience, 1992). For any active agents that may exist in enantiomeric forms, the active agent may be incorporated into the present compositions either as the racemate or in enantiomerically enriched form.

In cases where compounds are sufficiently basic or acidic to form acid or base salts, use of the compounds as salts may be appropriate. Examples of acceptable salts are organic acid addition salts formed with acids that form a physiologically acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

The compounds of the invention can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

It will be appreciated that compounds of the invention can be administered using various kinds of delivery systems and media. Furthermore, compounds of the invention can be administered in combination with other therapeutic agents and compounds and can be used with other kinds of treatments.

Pharmaceutical compositions that are useful in the methods of the invention may be administered systemically in oral solid formulations, ophthalmic, suppository, aerosol, injectable, topical or other similar formulations.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally, the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface-active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

In another specific embodiment, the aerosol formulation is a liquid aerosol formulation further comprising a pharmaceutically acceptable diluent, such as, but not limited to, sterile water, saline, buffered saline and dextrose solution.

The present invention contemplates pulmonary administration through an inhaler.

The composition may be formulated with a "mucosal penetration enhancer," i.e., a reagent that increases the rate or facility of transmucosal penetration, such as, but not limited to, a bile salt, fatty acid, surfactant or alcohol. In specific embodiments, the permeation enhancer can be sodium cholate, sodium dodecyl sulphate, sodium deoxycholate, taurodeoxycholate, sodium glycocholate, dimethylsulfoxide or ethanol.

As used herein, the term "inhaler" refers both to devices for nasal and pulmonary administration of a drug, e.g., in solution, powder and the like. For example, a the term "inhaler" is intended to encompass a propellant driven inhaler, such as is used for to administer antihistamine for acute asthma attacks, and plastic spray bottles, such as are used to administer decongestants.

Capsules, blisters and cartridges for use in an inhaler or insufflator may be formulated to contain a powder mix of the pharmaceutical compositions provided herein; a suitable powder base, such as lactose or starch; and a performance modifier, such as 1-leucine, mannitol, or magnesium stearate. The lactose may be anhydrous or in the form of the monohydrate. Other suitable excipients include dextran, glucose, maltose, sorbitol, xylitol, fructose, sucrose, and trehalose. The pharmaceutical compositions provided herein for inhaled/intranasal administration may further comprise a suitable flavor, such as menthol and levomenthol, or sweeteners, such as saccharin or saccharin sodium.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate, and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze-drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of a compound(s) in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg body weight of the recipient, from about 10 to about 75 mg/kg, about 3 to about 50 mg/kg, about 6 to 90 mg/kg, and about 15 to 60 mg/kg. In one aspect, a dose is about 1, 2, 3, 4, 5, 6, 7, 8, 9, 10, 11, 12, 13, 14, 15, 16 17, 18, 19, 20, 21, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 540, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg/kg. Administration can be per day, per treatment, or per procedure. In one aspect, more than one dose can be administered or a dose can be broken up into smaller sub-unit doses.

A compound can be conveniently administered in unit dosage form; for example, containing 5 to 1000 mg, conveniently 10 to 750 mg, most conveniently, 50 to 500 mg of active ingredient per unit dosage form.

In one embodiment, when the active ingredient needs to enter circulation and be delivered via blood, the active ingredient, can be administered to achieve peak plasma concentrations of the active compound of from about 0.5 to about 75 about 1 to 50 and about 2 to about 30 µM. This may be achieved, for example, by the intravenous injection of a 0.05 to 5% solution of the active ingredient, optionally in saline, or orally administered as a bolus containing about 1-100 mg of the active ingredient.

Desirable blood levels may be maintained by continuous infusion to provide doses at a particular mg/kg/hr or by intermittent infusions containing a selected amount (mg/kg) of the active ingredient(s).

The desired dose may conveniently be presented in a single dose or as divided doses administered at appropriate intervals, for example, as two, three, four or more sub-doses per day or per procedure. The sub-dose itself may be further divided, e.g., into a number of discrete loosely spaced administrations.

The composition of the invention can further comprise additional therapeutic additives, alone or in combination (e.g., 2, 3, or 4 additional additives). Examples of additional additives include but are not limited to: (a) antimicrobials, (b) steroids (e.g., hydrocortisone, triamcinolone); (c) pain medications (e.g., aspirin, an NSAID, and a local anesthetic); (d) anti-inflammatory agents; and (e) combinations thereof.

The method of the invention includes a kit comprising a compound identified in the invention and an instructional material which describes administering the compound or a composition comprising the compound to a cell or a subject to any target of interest, such as a surface. This should be construed to include other embodiments of kits that are known to those skilled in the art, such as a kit comprising a (preferably sterile) solvent suitable for dissolving or suspending the composition of the invention prior to administering the compound to a cell or a subject. Preferably the subject is a human.

In accordance with the present invention, as described above or as discussed in the Examples below, there can be employed conventional chemical, cellular, histochemical, biochemical, molecular biology, microbiology, and in vivo techniques which are known to those of skill in the art. Such techniques are explained fully in the literature.

Without further description, it is believed that one of ordinary skill in the art can, using the preceding description and the following illustrative examples, make and utilize the compounds of the present invention.

The invention is now described with reference to the following Examples and Embodiments. Without further description, it is believed that one of ordinary skill in the art can, using the preceding description and the following illustrative examples, make and utilize the present invention and practice the claimed methods. The following working examples therefore, are provided for the purpose of illustration only and specifically point out the preferred embodiments of the present invention, and are not to be construed as limiting in any way the remainder of the disclosure. Therefore, the examples should be construed to encompass any and all variations which become evident as a result of the teaching provided herein.

The present invention further provides kits. Kits of the invention comprise at least one compound of the invention and an instructional material for the use thereof, and optionally an applicator.

EXAMPLES

Example 1—Use of Neuroactive Steroids as Peripheral Analgesics and for Post-Operative Pain Background Sensitization of pain responses. Nociceptors can become hyperexcitable (sensitized) by various mechanisms in the presence of peripheral tissue injury. Individual nociceptors that have been sensitized can be activated by stimuli that previously would not have been intense enough to cause activation (allodynia), as well as by previously noxious stimuli that now produce an even greater sensation of pain (hyperalgesia). The electrophysiological correlates of this altered evoked pain response include a lowered threshold for nociceptor activation and increased frequency of firing in response to a suprathreshold stimulus, respectively. Furthermore, clinical symptoms of spontaneous pain can be directly correlated to the spontaneous spike firing in nociceptors. Peripheral sensitization often leads to central sensitization, or increased synaptic efficacy and spontaneous activity of DH neurons in the spinal cord. Recent animal and human studies have shown that symptoms of stimulus evoked pain (thermal and mechanical hyperalgesia), as well as spontaneous pain symptoms such as guarding are prominent after surgical procedures. Acute painful episodes from surgical skin incision and deep tissue injury are generally responsive to conventional treatments like opioids and regional anesthesia with local anesthetics. However, these treatments are not suitable for longer treatments due to side effects such as numbness and muscle weakness from local anesthetics, and respiratory depression, tolerance, and addiction from the excessive use of opioids. In addition, it has been well established that long-term use of opioids leads to a heightened pain sensitivity stage termed opioid-induced hyperalgesia, and this can paradoxically increase postoperative pain. Thus, further mechanistic studies of sensitization of postoperative pain responses manifested as hyperalgesia, allodynia, and spontaneous pain are warranted.

Voltage-gated Ca2+ channels (VGCCs). Several subtypes of VGCCs are expressed in neurons in the pain pathway and are crucial not only in shaping action potentials, but also in controlling cellular excitability and synaptic transmission in these cells. On the basis of the membrane potential at which they become activated, VGCCs are subdivided into two major classes: high-voltage-activated (HVA) or sustained currents and low-voltage-activated (LVA) or transient (T-type) $Ca^{2+}$ currents (Catterall, 2000). These channels are products of different genes, which give rise to α1 subunits that form the pores of the VGCCs named the $Ca_v1$ family (former α1S, α1C, α1D, α1F) encoding L-type; $Ca_v2.1$ (α1A) encoding P/Q-type; $Ca_v2.2$ (α1B) encoding N-type; and $Ca_v2.3$ (α1E) encoding R-type which activate at more negative potentials than other HVA channels. It is well established that N-type channel blockers have a major function in presynaptic inhibition in the DH of the spinal cord and clinical studies are under way to establish their utility in treatments of patients with intractable pain. In addition, animal studies with $Ca_v2.3$ knockout (KO) mice and $Ca_v2.1$ KO mice have shown abnormal pain responses, suggesting that these channels also contribute to nociceptive sensory transmission. However, due to paucity of selective R-type blockers the role of these channels in nociceptive signaling remains poorly understood. Cloning of pore-forming al subunits of T-channels has shown the existence of at least three subtypes: G ($Ca_v3.1$), H ($Ca_v3.2$), and I ($Ca_v3.3$). Many recent studies have established that $Ca_v3.2$ T-channels contribute to nociceptive sensitization. Clinical phase II trial studies by pharmaceutical companies (Zallicus, Abbot) are underway to determine the usefulness of selective T-channel blockers for the treatment of pain disorders.

Neuroactive steroids are potent peripheral analgesics. The neuroactive steroids are potent modulators of neuronal activity in the peripheral and central nervous system by causing a variety of behavioral and neuroendocrine changes in humans and animals (e.g., general anesthesia, analgesia, cognitive and mood disturbances). It is believed that effects on neurosensory processing and neuronal excitability are primarily mediated by actions at various ligand-gated ion channels, with much attention focused on the modulation of γ-aminobutyric acid (GABAA) receptors by steroids such as alphaxalone (3α,5α)-3-hydroxypregnane-11,20-dione (FIG. 1). However, we have found that a neuroactive steroid with a 5α configuration at the steroid A,B ring fusion [(+)-ECN] [(3β,5α,17β)-17-hydroxyestrane-3-carbonitrile] (see structure on FIG. 1), is a potent voltage-dependent blocker of T-channels in rat DRG neurons ($IC_{50}$ of 300 nM, maximal block 40% current). ECN only weakly inhibits recombinant $Ca_v2.3$ currents ($IC_{50}$ 16 μM) and has very little effect on voltage-gated Na+, K+, N- and L-type HVA $Ca^{2+}$ channels, glutamate and GABA-gated channels (Todorovic et al., 1998). Furthermore, it is known that analgesic potency of alphaxalone, ECN, and related 5α-reduced steroids is correlated to their ability to potentiate GABAA-gated currents and/or inhibit T-currents in DRG neurons. We have also previously identified several synthetic 5β-reduced steroid analogues that lack any direct effect on GABAA currents but potently and completely inhibit T-currents in DRG cells and exhibit potent local analgesic effect in vivo (Todorovic et al., 2004). One of the most potent steroid analogues in this group, 3β-OH ((3β,5β,17β)-3-hydroxyandrostane-17-carbonitrile) (FIG. 1) is a voltage-dependent and selective blocker of T-currents in acutely dissociated DRG cells ($IC_{50}$ 3 μM, 100% maximal block). CDNC24 ((3α,5α)-3-hydroxy-13, 24-cyclo-18,21-dinorchol-22-en-24-ol) has no effect on T-currents in DRG cells but is a potent potentiator of GABAA currents and is an anesthetic in tadpoles. Compounds like CDNC24 will be useful in studies to separate the role of GABAA channels vs. VGCCs.

Ion channels as targets for anesthetic agents. Most of the clinically used GAs either inhibit N-methyl-D-aspartate (NMDA) mediated excitatory currents in CNS (e.g. ketamine, nitrous oxide) and/or potentiate γ-amino-butyric acid (GABA)A-mediated inhibitory currents (e.g., isoflurane, propofol, etomidate). Unfortunately, data from in vivo animal models and humans indicate that clinically used GAs that interact with GABAA and NMDA channels are neurotoxic to the developing mammalian brain and have implicated GAs in causing cognitive deficits later in life (Jevtovic-Todorovic and Olney, 2008; Wilder et al., 2009). Previous studies have shown that T-channels and R-channels in thalamic circuitry are inhibited by clinically relevant concentrations of isoflurane.

The present application describes investigation of a neuroactive steroid 3β-OH, which is a potent T-channel and R-channel blocker devoid of any direct effects on postsynaptic GABAA and NMDA currents. This is important since currently used injectable GAs that potentiate GABAA currents (e.g. propofol and etomidate) have very modest analgesic properties and another injectable anesthetic and NMDA blocker ketamine, is a good analgesic but it has significant side effects including cognitive impairment and psychosis.

Example 1 Results 1. 5β-Reduced Neuroactive Steroids that are Potent Blockers of $Ca_v3.2$ T-Channels and Devoid of any GABA-Mimetic Properties are Good Hypnotics in Young Rodents.

We previously reported that 3β-OH inhibits T-currents in nucleus reticularis thalami (nRT) (IC50 2 μM Joksovic et al., 2007) with potency similar to that found in DRG cells (IC50 3 μM). Since T-channels in nRT play an important role in thalamocortical oscillations that govern awake and sleep cycle (Crunelli et al., 2014), we examined possible hypnotic effects of 3β-OH.

Figure 2:
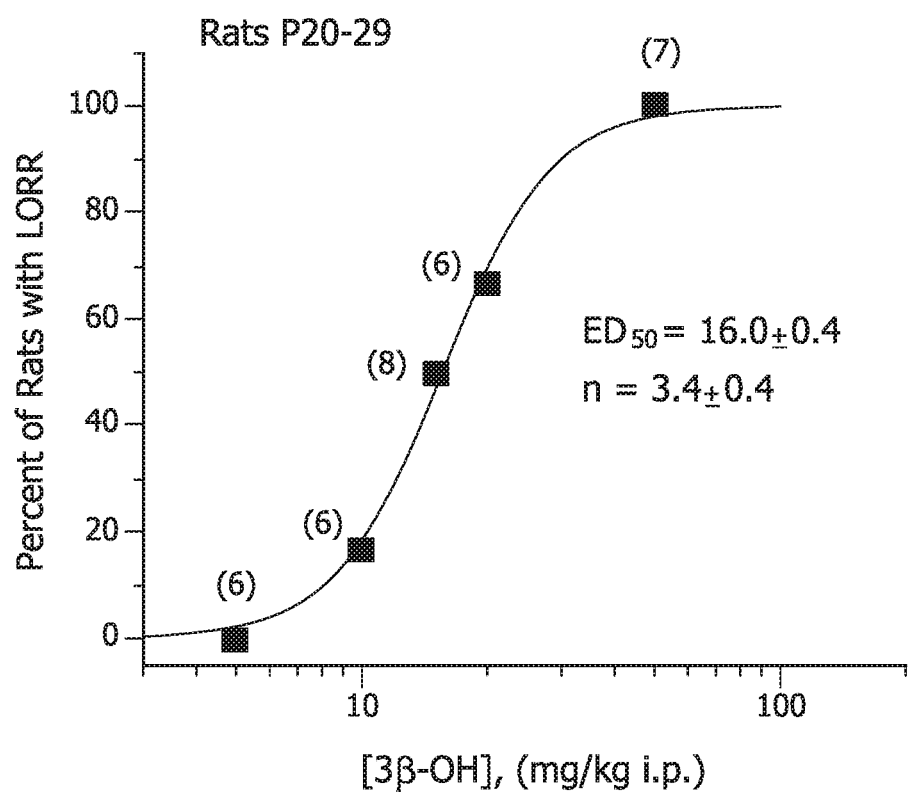
FIG. 2. 3β-OH induces LORR in young rats.

For in vivo experiments, steroids were freshly dissolved in 15% β-cyclodextrin solution and injected intraperitoneally (i.p.) at escalating doses from 5 to 75 mg/kg. We found that in young adolescent rats of both sexes at postnatal age days 20-29 (P20-29) 3β-OH induced loss of righting reflex (LORR) with an estimated $ED_{50}$ of 16.0±0.4 mg/kg (with slope of 3.4±0.4 (FIG. 2, n=33 rats, in parenthesis in FIG. 2 are indicated number of rats per data point). Solid red line on FIG. 2 is the best fit using Hill-Langumir equation $P_{LORR}$ ([3β-OH])=$P_{LORRmax}/(1+(IC_{50}/[3β-OH])^h)$ where $P_{LORRmax}$ is the maximal percent of animals with LORR, $ED_{50}$ is the dose that produces 50% effect, and h is the apparent Hill-Langmuir coefficient for the effect. Using the same methods, we also found that 3β-OH induced LORR in adult female C57Bl/6 mice with an ED50 of 46±2 mg/kg (n=26 mice, data not shown). LORR in these animals lasted up to 50 min for a 75 mg/kg dose. The present invention further encompasses the administration of 3β-OH and related neurosteroids injected i.p. as useful analgesics for postoperative pain.

2. The Role of $Ca_v3.2$ T-Channels and Neuroactive Steroids in Spinal Pain Processing.

Figure 3:
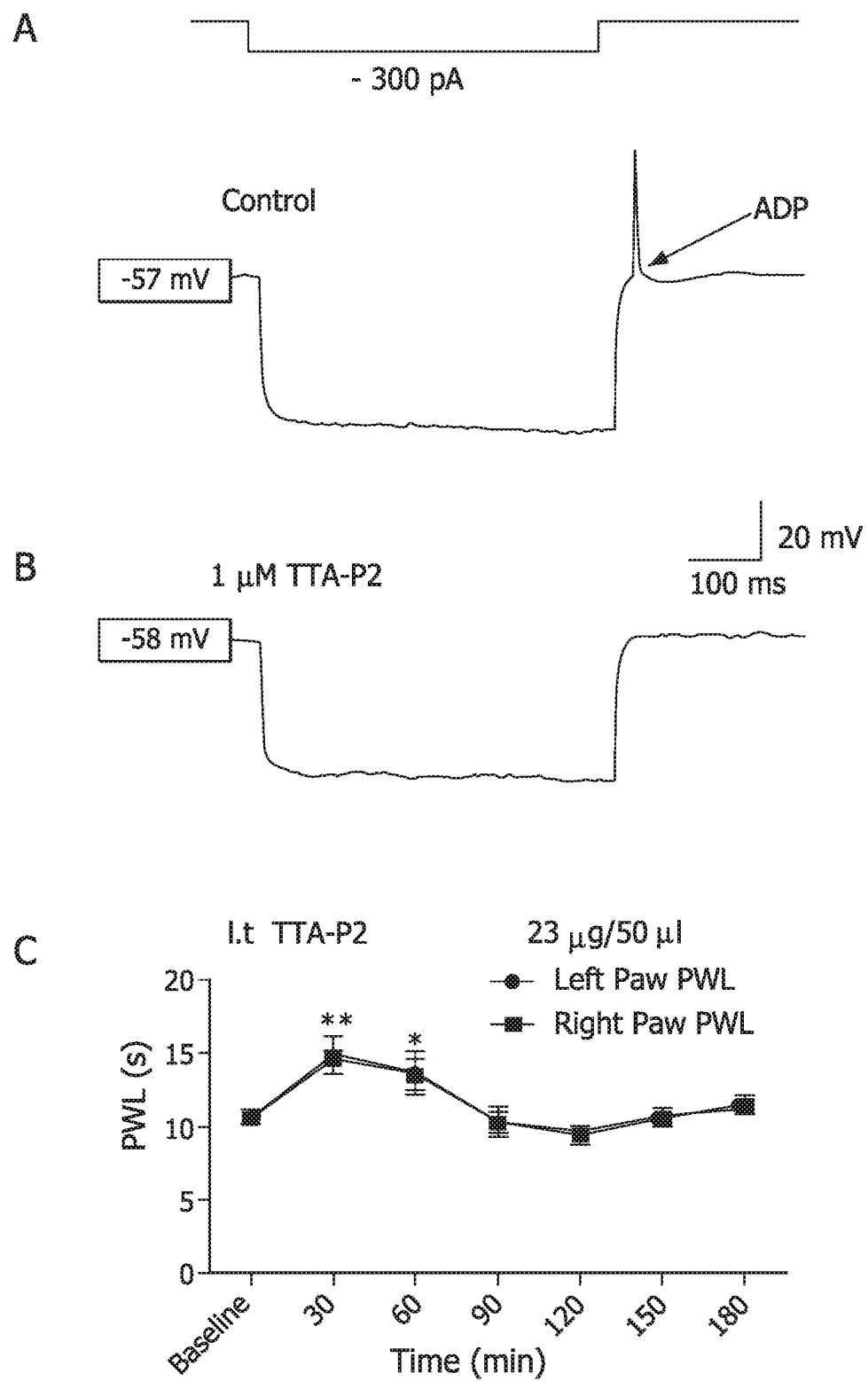
FIG. 3. TTA-P2 inhibits ADP and rebound AP firing in lamina I DH neurons and induces spinally-mediated analgesia.
Figure 4:
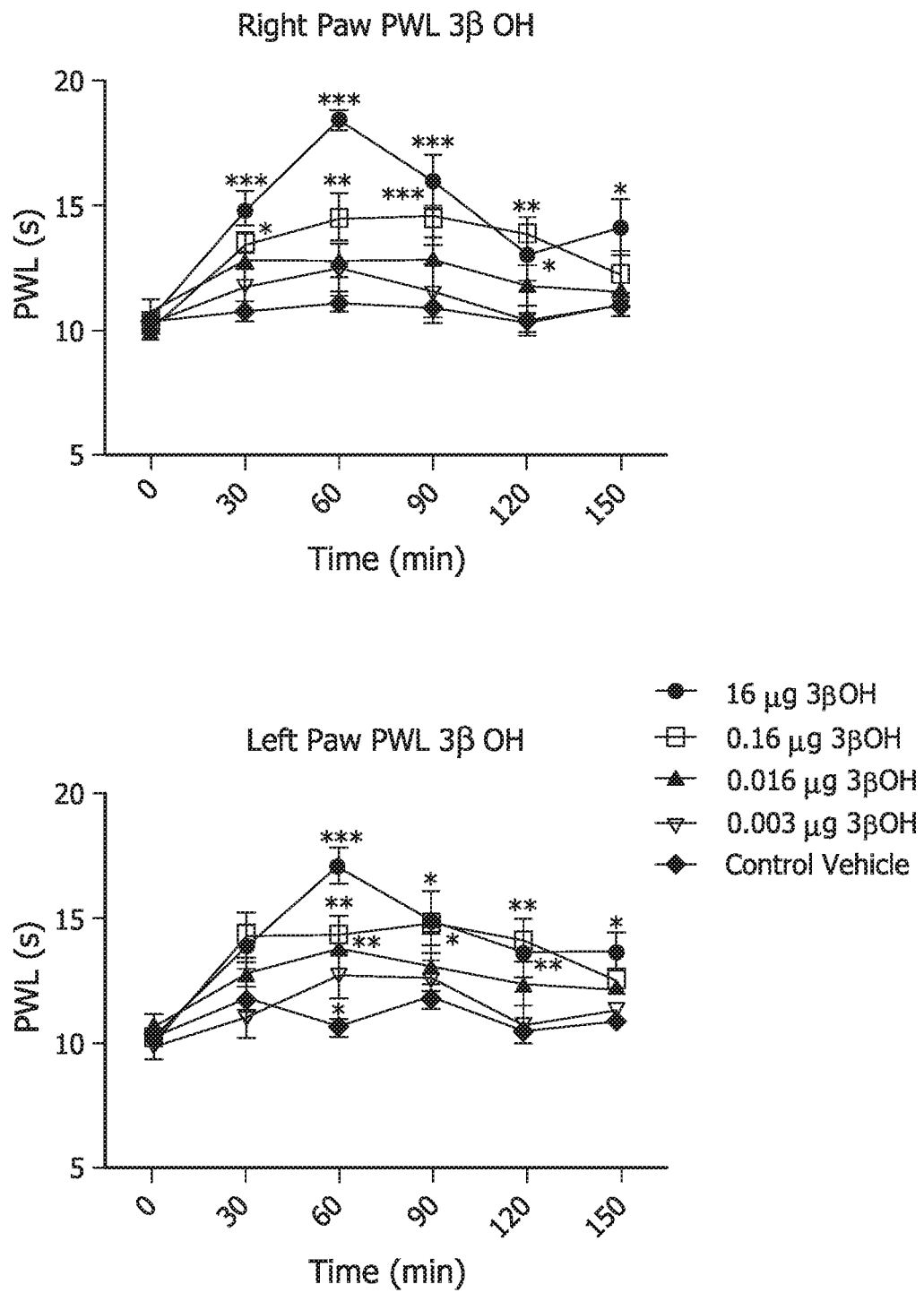
FIG. 4. 3β-OH induces potent spinally-mediated analgesia in naïve rats. n=7-9 rats per group. *, $p<0.05$; , $p<0.01$; *, $p<0.001$ compared with vehicle by one-way ANOVA with repeated measures.

The central processes of most nociceptive sensory neurons terminate in superficial layers of the Dorsal Horn (DH) (laminae I and II) of the spinal cord, an important pain processing and integration region. In the DH, glutamate is a fast excitatory transmitter that mediates much of the nociceptive signaling and may be responsible for induction of central sensitization associated with altered nociception. It is known that in addition to Cav3.2 channels, Cav2.3 channels contribute to spontaneous excitatory transmission in nociceptive DH neurons.

a. Selective T-channel blocker TTA-P2 diminishes cellular excitability in DH neurons in vitro and exhibits spinally-mediated analgesia in vivo. We began by studying the role of postsynaptic T-channels in DH neurons using current-clamp recording from unidentified lamina I-II DH neurons in spinal cord slices in vitro. To exclude synaptic currents, our external solution contained 20 µM picrotoxin, 50 µM d-APV and 5 µM NBQX to block inhibitory and excitatory synaptic currents, respectively. We first injected −300 pA of current via the recording electrode for 500 ms, which hyperpolarized the resting membrane potential (RMP) and allowed T-channels to recover from inactivation. This protocol served to assess input resistance ($R_{in}$) and to evoke rebound action potential (AP) firing. The top line in FIG. 3A depicts the protocol of current injection while bottom traces represent membrane responses. After injecting a hyperpolarizing current, the cell exhibited an after-depolarizing potential (ADP) and rebound AP firing (arrow on FIG. 3B, top trace). We then applied 1 µM TTA-P2 in the external solution for 5 minutes and repeated the same recording protocol (FIG. 3B, bottom trace). It is evident that blocking T-channels with TTA-P2 had very little effect on baseline RMP and the amplitude of hyperpolarized membrane responses, but completely inhibited ADP and a rebound AP. This finding was consistent in all DH cells challenged with TTA-P2: control: 1.25±0.25 APs; TTA-P2; 0±0 APs (n=4, p<0.05). In contrast, there was very little effect of TTA-P2 on RMPs (control: −57±2 mV; TTA-P2: −58±3 mV; p>0.05) or $R_{in}$ (control: 194±37 MΩ; TTA-P2: 191±29 MΩ; p>0.05). Overall, these data strongly suggest a role for postsynaptic T-channels in the excitability of DH neurons. To investigate the possible role of T-channels in spinal nociceptive transmission in vivo, we used intrathecal (i.t.) injections and measured thermal nociceptive responses to noxious heat in adult naïve rats using methods as we described elsewhere (Messinger et al., 2009; Obradovic et al., 2014, PLoS ONE 9(4): e91467. doi:10.1371/journal.pone.0091467). For i.t. injections, rats were briefly anesthetized with 1.5-2% isoflurane and thermal paw withdrawal latencies (PWLs) were measured starting from 30 minutes following injection. FIG. 3C summarizes our results and demonstrates for that TTA-P2 (23 µg in 50 µL of 15% β-cyclodextrin vehicle, i.t.) significantly increased thermal PWLs up to 50% from baseline (pre-injection values) in both paws as measured 30 and 60 minutes post injection (n=6 rats, one-way ANOVA, *p<0.05, **p<0.01). After 90 minutes, thermal PWLs in both paws returned to near baseline levels and remained stable up to 180 minutes of recording. In contrast, injections of vehicle alone did not alter baseline PWLs (n=7 rats, data not shown).

b. 3β-OH induces potent dose-dependent spinally-mediated analgesia in naïve rats. To assess its potential for spinally mediated analgesia, we injected 4 escalating doses of 3β-OH i.t. (from 0.003 to 16 µg) dissolved in 50 µL of vehicle (15% β-cyclodextrin) and measured thermal PWLs at 30 minutes intervals up to 150 minutes after injections. FIG. 4 shows that 3β-OH effectively induced dose-dependent prolongation of PWLs in the right paws (upper panel) and left paws (lower panel) by up to 80% over pre-injection baseline values when measured at 60 minutes post-injections. The analgesic effect was long-lasting, with higher doses of 3β-OH increasing PWLs by about 25-30% at 150 minutes post-injections. Note that PWLs remained stable in both paws during injections of vehicle (red lines). We also considered the possibility that i.t. injected 3β-OH may non-specifically affect performance by decreasing motor strength and/or coordination. Hence, we performed a battery of sensorimotor tests focused on agility and fine motor abilities as we published elsewhere (Latham et al., Diabetes. 2009 November; 58(11):2656-65. doi: 10.2337/db08-1763. Epub 2009 Aug. 3.). Rats (n=6), were tested using an inclined plane, platform, and ledge before injection of the highest dose of 3β-OH (16 µg i.t.) and at 60 min after injection, corresponding to the time of maximal analgesia (FIG. 4). The responses after treatment with 3β-OH in these animals did not differ significantly from those before injection on any of these tests, suggesting that the analgesic effect of 3β-OH likely is mediated by targets located in the pain pathways (data not shown).

3. Intrathecal Applications of 3β-OH Attenuate Development of Thermal Hypersensitivity after Skin and Deep Tissue Incision in Rats.

Figure 5:
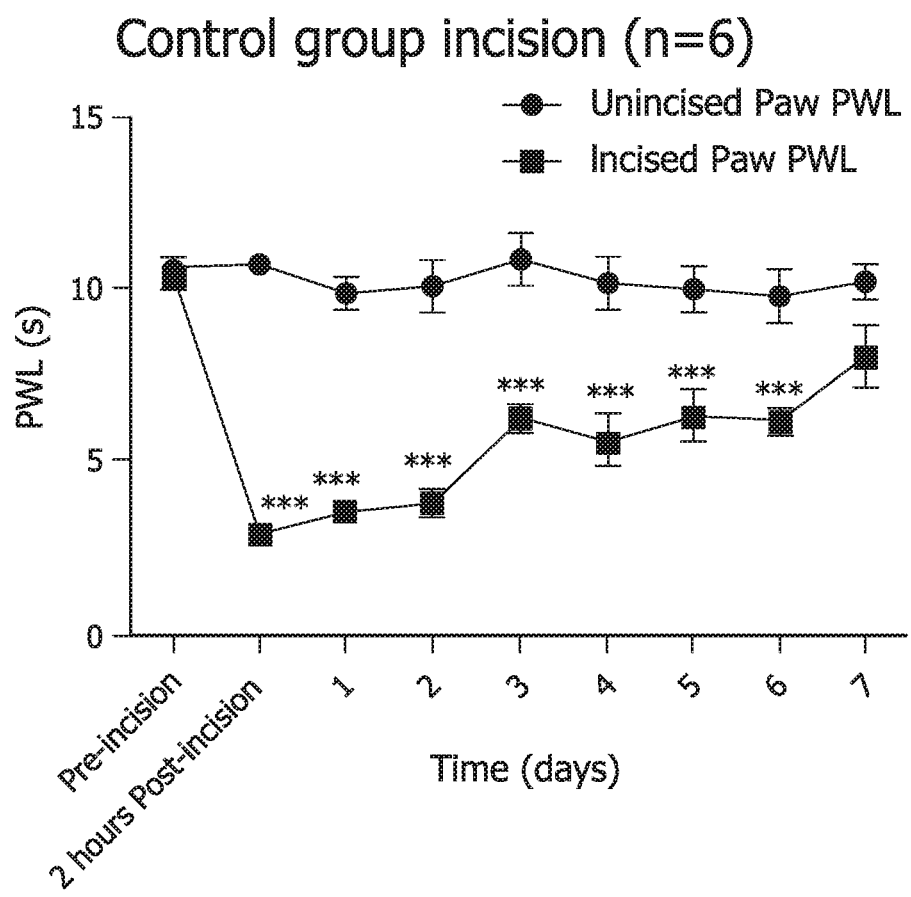
FIG. 5. Development of thermal hyperalgesia following skin and deep tissue incision in rats. ***, $p<0.001$ when compared unincised vs. incised paws by one-way ANOVA with repeated measures (n=6 rats per group).

In order to study the potential role of neuroactive steroids in perioperative analgesia we used a model of a plantar incision of skin and deep tissue in the hind paw of rats. Starting 2 hours after operation, thermal hyperalgesia to nociceptive heat stimuli was assessed measuring thermal PWLs. As depicted in FIG. 5, thermal hyperalgesia is profound up to two days after surgery as evidenced by attenuated PWLs in incised (right) paws by about 70% when compared to unincised (left) paws in the same animals. This gradually resolved and returned to near preoperative baseline values within 7 days. Note that thermal PWLs in unincised paws remained stable during this period.

Figure 6A:
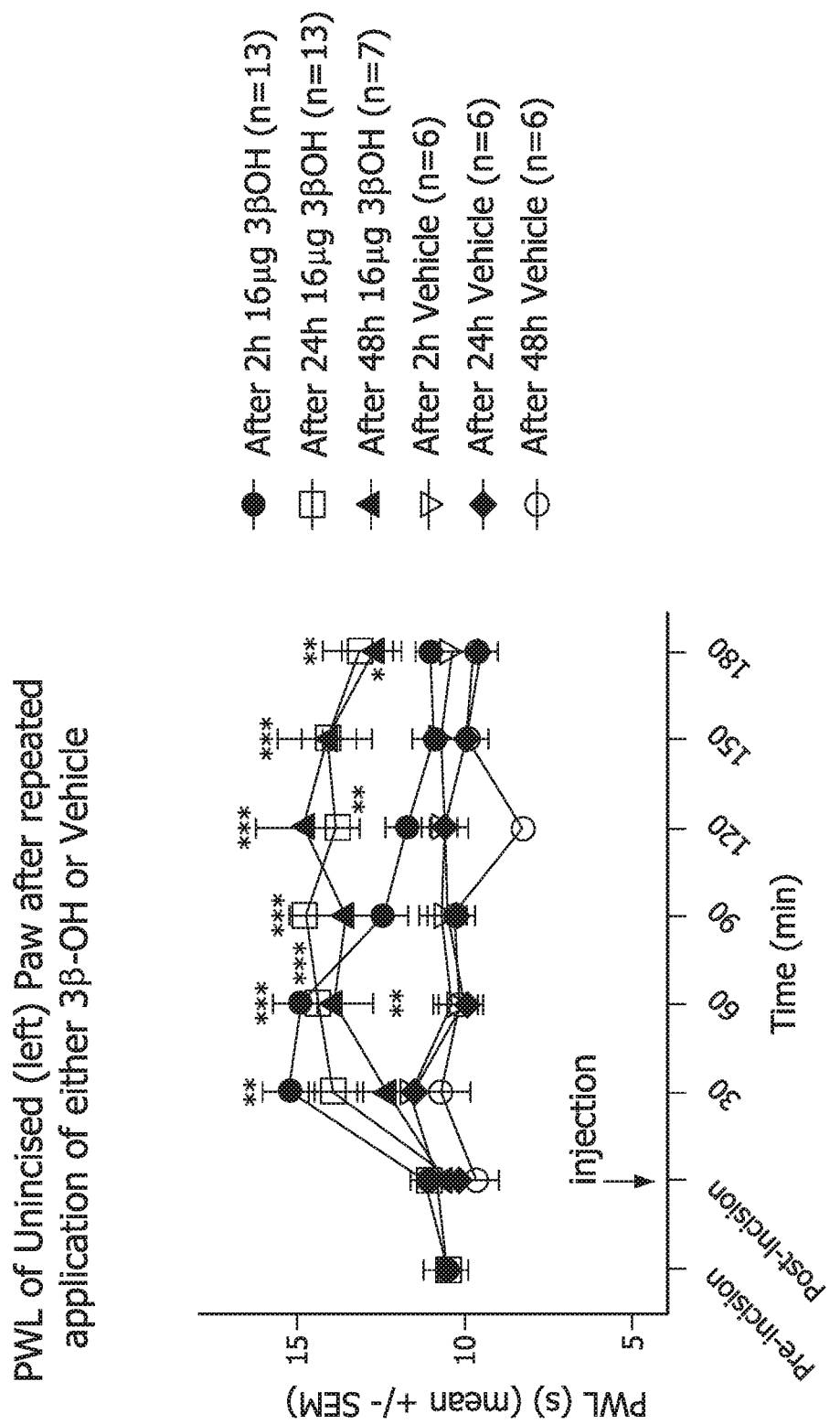
FIG. 6. 3β-OH injected i.t. attenuated incision-induced thermal hyperalgesia. Number of animals per group are indicated in parenthesis. *, $p<0.05$; , $p<0.01$; *, $p<0.001$ when compared to appropriate vehicle group (two-way ANOVA with repeated measures).
Figure 6B:
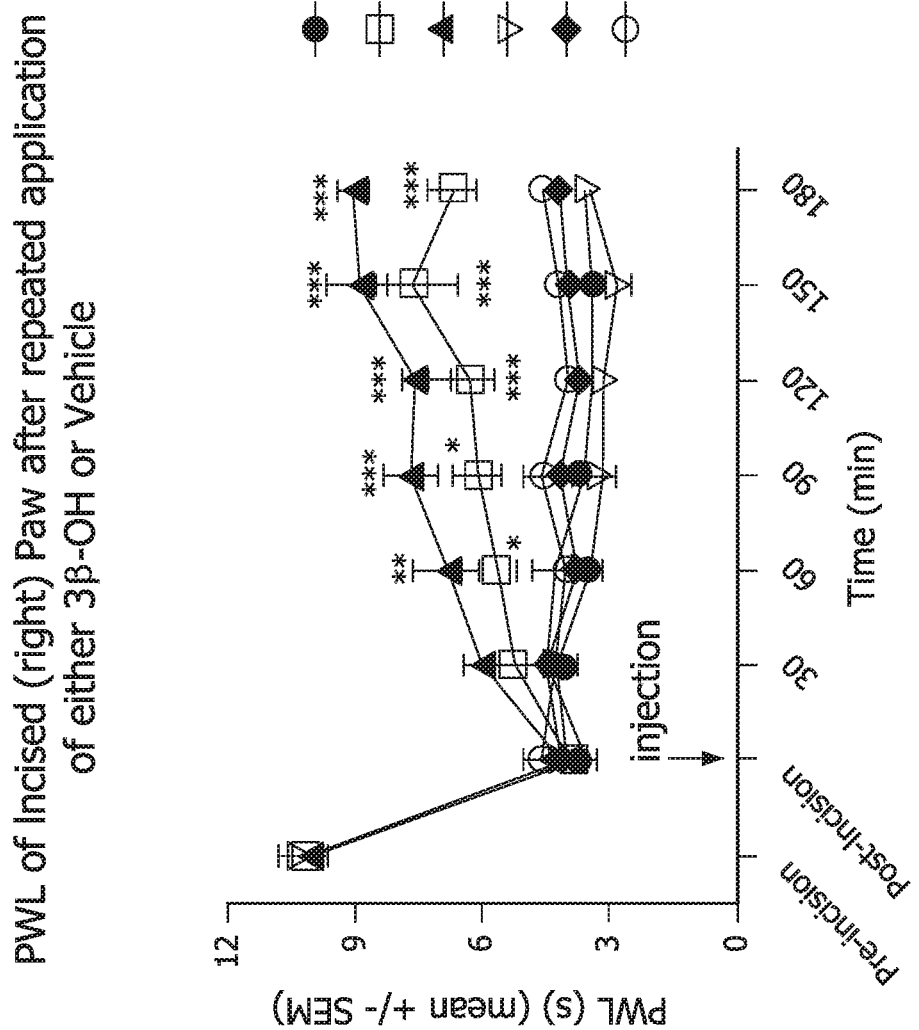

Next, we examined the ability of 3β-OH to influence thermal hyperalgesia in this rat model of perioperative pain. Because FIG. 4 shows that in healthy un-operated rats this steroid induced dose dependent spinally-mediated analgesia with an apparent maximal effect at 16 µg, we used this dose in ensuing experiments in rats with skin and deep tissue incision. We applied the same dose of steroid or vehicle i.t. at 2, 24 and 48 hours after surgery and measured thermal PWLs in both paws (unincised paws, top panel of FIG. 6; incised paws, bottom panel of FIG. 6) at 30 minute intervals from 30-180 minutes after surgery in order to assess the time course and possible tolerance to any analgesic and antihyperalgesic effect of 3β-OH. FIG. 6 summarizes average results from multiple animals (6-13 per group). It is noteworthy that 3β-OH had little effect on thermal PWLs when compared to vehicle in incised paws when applied 2 hours after incision (bottom panel, filled round symbols) while in contralateral unincised paws (top panel, filled round symbols) the same dose induced analgesia at the 30 and 60 minute time points as evidenced by increased PWLs when compared to vehicle injections (top panel, filled circles). Furthermore, subsequent i.t. injections of 3β-OH at 24 hours (open squares) and 48 hours (filled triangles) induced long-lasting progressive anti-hyperalgesia in incised paws (bottom panel) with return of thermal PWLs to near baseline pre-incisional values measured at 180 minutes after injection (48 hours group). For example, at 48 hours post-surgery the average PWL of incised paws at 180 minutes post vehicle injection was about 4 seconds, while at 180 minutes post steroid injection PWLs were prolonged to about 9 seconds and approached pre-incisional values. In contrast, in unincised paws the same injections of 3β-OH induced analgesia of similar magnitude to the analgesia produced when steroid was injected 2 hours post-surgery, measuring in average 14-15 seconds on thermal PWLs (top panel).

4. Repeated i.pl. Injections of 3β-OH Attenuate Development of Thermal Hyperalgesia after Rat Paw Incision.

We next tested the idea that locally applied 3β-OH may abolish thermal hyperalgesia after paw incision. For these experiments we first obtained baseline (pre-incision) thermal PWLs (about 10 seconds) and repeated measurements 2 hours after surgery (about 2.5 seconds). We then injected (arrow on FIG. 7A) directly into the incised paw either 16 μg or 48 μg of 3β-OH in 100 μl of saline that was pH adjusted to 7.4 (n=6 rats in each group). We recorded PWLs for three consecutive days after injections. We found that the dose of 16 μg 3β-OH ameliorated thermal hyperalgesia at day 1 after incision as evidenced by significantly increased PWLs to about 6 seconds (*, black circular symbols, FIG. 7A). With this dose, PWLs at day 2 were not significantly different from the rats that received vehicle into incised paws (gray symbols, FIG. 7A).

Figure 7A:
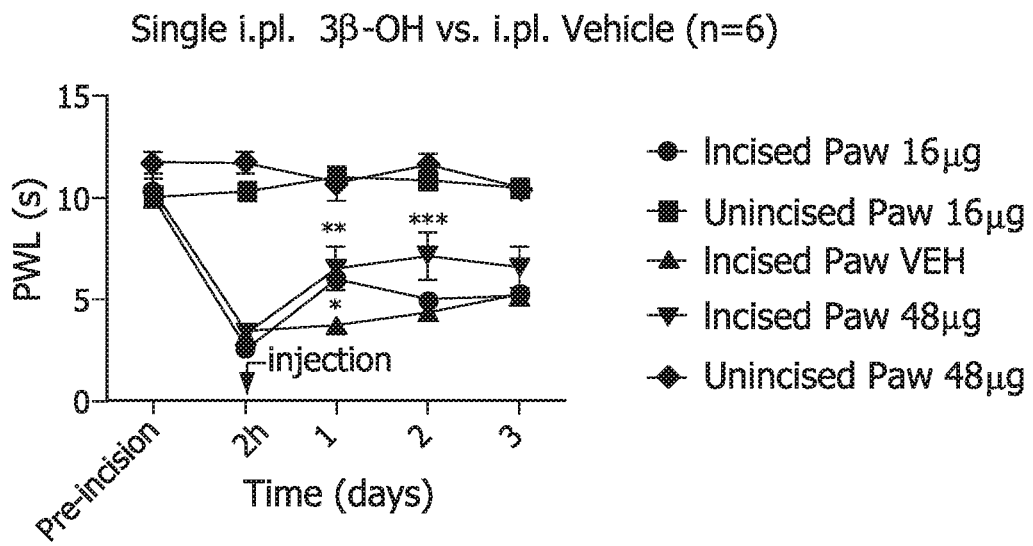
FIG. 7. 3β-OH injected i.pl. attenuated incision-induced thermal hyperalgesia. *, $p<0.05$; , $p<0.01$; *, $p<0.001$ when compared to appropriate vehicle group (two-way ANOVA with repeated measures).
Figure 7B:
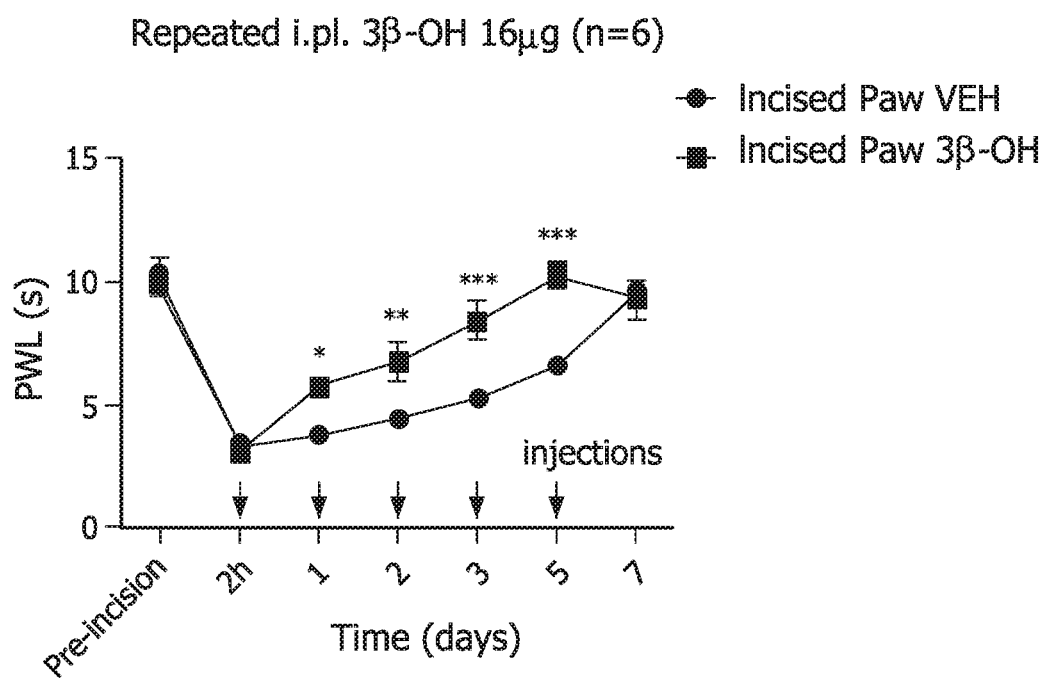

FIG. 7A also shows that with the single injected dose of 48 μg, 3β-OH relieved thermal hyperalgesia as evidenced by measured PWLs of about 6.5 seconds at day 1 (, $p<0.01$) and about 7 seconds on day 2 (*, $p<0.001$) post incision (red inverted triangles). Note that PWLs in noninjected (unincised) paws (black squares and red diamonds) remained stable indicating lack of any systemic effect. We next investigated if rats may exhibit tolerance to anti-hyperalgesic effect of 3β-OH. For these experiments depicted on FIG. 7B, we first obtained pre-incision PWLs, and then injected 16 μg of 3β-OH repeatedly at the following time points: 2 hours, day 1, 2, 3 and 5 after post-surgery (n=6 rats). As shown on FIG. 7B (red symbols) repeated injections of steroid induced progressive anti-hyperalgesia from day 1 to day 5 post surgery with increase in PWLs from 50-90% when compared to PWLs in incised paws injected with vehicle (*, $p<0.05$; , $p<0.01$; *, $p<0.001$). Overall, these experiments indicate that locally injected 3β-OH exhibits a prominent antihyperalgesic effect without apparent tolerance in the rats with paw incision.

5. 3β-OH inhibits recombinant $Ca_v2.3$ currents.

We previously showed that isoflurane inhibits Cav2.3 channels in the thalamocortical circuitry at clinically relevant concentrations and proposed that this effect may contribute to the hypnotic effect of GAs (Joksovic et al., 2009). Another study with KO mice also implicated Cav2.3 channels in nociception (Saegusa et al., 2000).

Figure 8A:
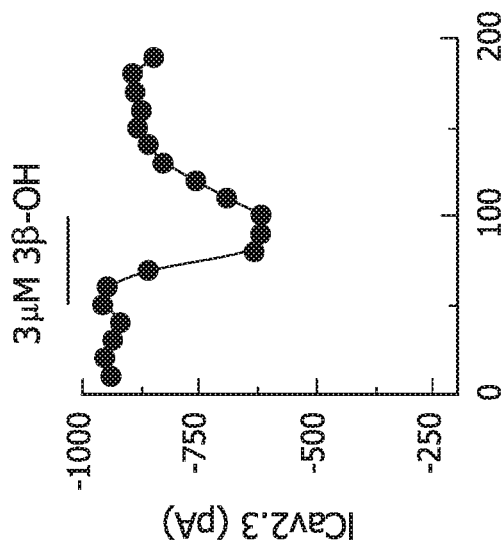
FIG. 8. 3β-OH and isoflurane inhibit recombinant human CaV2.3 currents. A: representative traces and B: time course of current inhibition by 3 μM 3β-OH. C: bar graph shows average data from multiple experiments. **, $p<0.01$ (t-test).
Figure 8B:
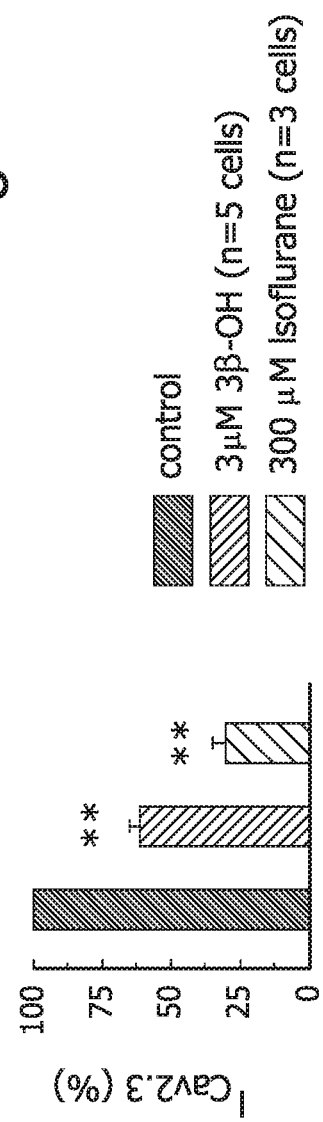
Figure 8C:
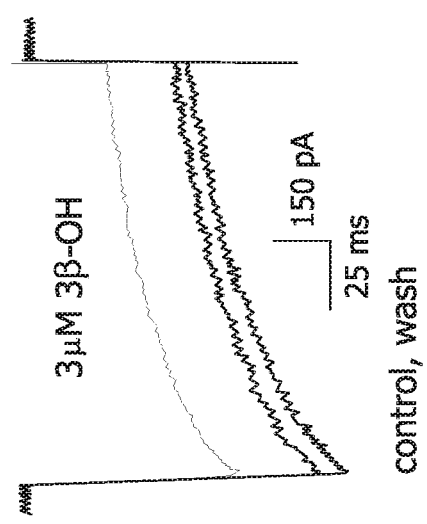

Here, we examined the sensitivity of recombinant human Cav2.3 channels stably expressed in human embryonic kidney (HEK) 293 cells to 3β-OH. FIGS. 8A and 8B show traces and a time course from a representative HEK 293 cell, indicating that 3β-OH also reversibly inhibited recombinant Cav2.3 currents. The bar graph in FIG. 8C shows that on average, 3β-OH (red bar) inhibited 38±4% of control pre-drug values (black bar) of recombinant Cav2.3 currents (n=5 cells, $p<0.01$). For comparison, the same graph in FIG. 8C (cross-hatch symbol) shows that 300 μM of isoflurane inhibited 69±4% of control pre-drug values of inward current. Hence, it appears that 3β-OH inhibits Cav3.2 and Cav2.3 channels with similar potency.

Example 2—Novel Neurosteroid Anesthetics and Developmental Synaptogenesis

Background: Animal studies demonstrate that general anesthesia during critical early stages of brain development could have devastating outcomes on neuronal function and cognitive development. Newly developing clinical studies also suggest an association between an early exposure to anesthesia and long-term behavioral impairments in humans. Because of the need to provide comfort to our children during painful procedures many of us have attempted to introduce a variety of 'safening' strategies, which are turning out to be of questionable or unknown long-term benefit and even more questionable clinical relevance.

All currently used general anesthetics are potent modulators of γ-aminobutyric acid A $(GABA)_A$ receptors (e.g. propofol, barbiturate, benzodiazepines, sevoflurane, isoflurane) and/or N-methyl-D-aspartate (NMDA) receptors (e.g. ketamine, nitrous oxide) and are neurotoxic during early stages of development. Although causality between $GABA_A$ potentiation or NMDA blockade and anesthesia-induced developmental neurotoxicity requires further study, disclosed herein are anesthetics having different cellular targets that are not neurotoxic compared to currently used general anesthetics. Because T-type channels activate with small membrane depolarizations, they play a crucial role in controlling sensory neuron excitability.

Example 2 Results

Although no preclinical data are currently available on the long-term use of 3β-OH, ECN, and related neuroactive steroids, previous evaluation of the safety of non-steroidal blockers of T-channels such as TTA compounds in dogs has disclosed no cardiovascular side effects. Furthermore, in a preliminary study with acute applications of anesthetic doses of 3β-OH in adult monkeys we did not notice cardiac arrhythmias (data not shown).

Figure 9A:
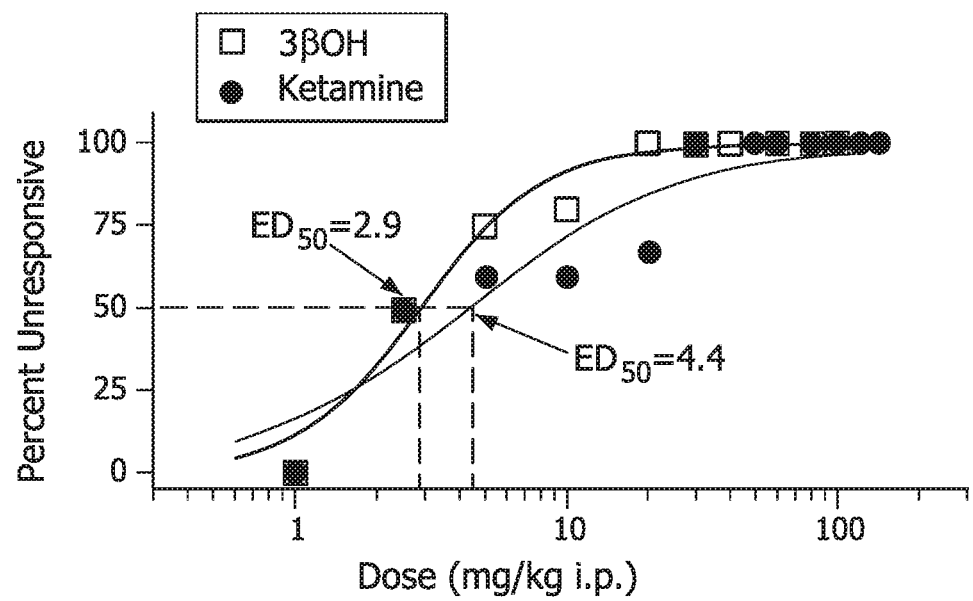
FIG. 9, comprising A, B, and C, graphically depicts the anesthetic properties of 3β-OH and ketamine by measuring the loss of right reflex (LORR).
Figure 9B:
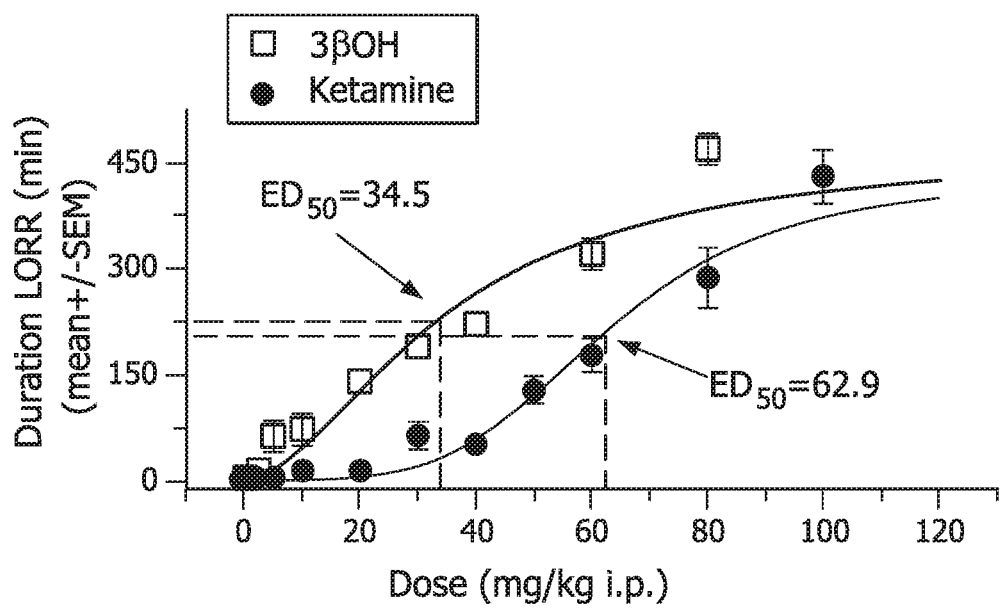
Figure 9C:
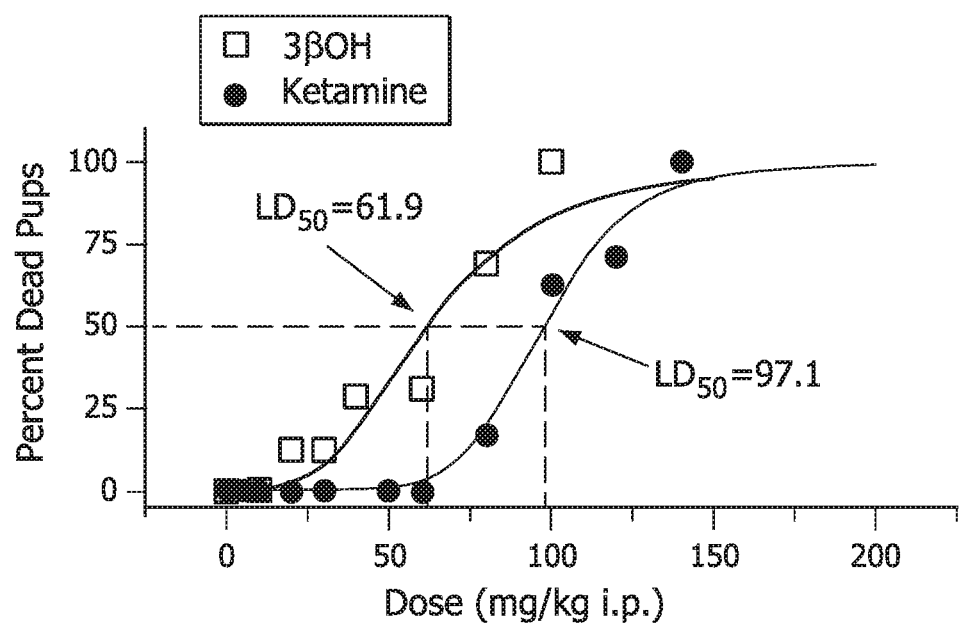

1. Characterization of Activity of Neuroactive Steroid Analogs:

To begin to understand the hypnotic properties of T-channel-blocking steroid analogs, we examined the anesthetic effects of a representative neuroactive steroid, 3β-OH (FIG. 9), by measuring the loss of righting reflex (LORR) after i.p. administration in rat pups (at post-natal day 7-PND7). The LORR with 3β-OH was compared with a clinically used injectable anesthetic, ketamine. 3β-OH was freshly dissolved in 15% cyclodextrin solution (vehicle) and injected i.p. at doses from 1 to 100 mg/kg; ketamine was dissolved in saline and injected i.p. at doses from 1 to 140 mg/kg. After either 3β-OH or ketamine was administered, rat pups were turned onto their backs and anesthesia (i.e. 'unresponsiveness') was defined as the inability to turn back over onto all 4 legs ("right themselves") within 5-10 seconds. The percent of rat pups that were unresponsive were recorded at each dose (shown on y-axis). Each rat pup received only one dose shown on x-axis. As shown in FIG. 9A calculated ED50 for LORR is 2.9±0.28 mg/kg with 3β-OH and 4.4±0.95 mg/kg with ketamine (n=3-10 pups per data point). The solid line was obtained using the Hill-Langumir equation. The onset of anesthesia with 3β-OH was in a matter of several minutes (2 to 9 minutes) and comparable to ketamine (1 to 7 minutes). The duration of LORR with 3β-OH or ketamine, as shown in FIG. 9B, was dose-dependent reaching over 400 minutes with the highest doses. At any given dose 3β-OH exhibited longer duration of LORR than did ketamine, suggesting higher efficacy. Calculated $EC_{50}$ was 34.5±3.7 mg/kg for 3β-OH and 62.9±3.9 mg/kg for ketamine, suggesting higher potency as well. In control experiments, i.p. injections of the same volumes of either 15% cyclodextrin or saline alone did not cause LORR. To assess how the therapeutic index of 3β-OH compares to that of ketamine, we calculated the $LD_{50}$ for each anesthetic based on the response curve shown in FIG. 9C. The dose response curve for both anesthetics was rather steep with the LD50 of 61.9±4.6 mg/kg for 3β-OH and 97.1±1.98 mg/kg for ketamine, thus resulting in comparable therapeutic index of about 22 for both 3β-OH and ketamine. The $LD_{50}$ was calculated using the Hill-Langumir equation and is shown in FIG. 9C.

2. T-Channel Blocking Neuroactive Steroid Analogs do not Cause Morphological and Biochemical Impairments of Synaptogenesis, the Hallmarks of Anesthesia-Induced Developmental Neurotoxicity.

Background: Early exposure to commonly used general anesthetics causes extensive and widespread apoptotic neurodegeneration. Numerous studies have shown that activation of a caspase-3-dependent cascade is what ultimately leads to DNA fragmentation and neuronal death. Although both the intrinsic and extrinsic apoptotic pathways are activated, the intrinsic pathway that is mitochondria-dependent appears to be the initial and most sensitive activator of anesthesia-induced developmental neuroapoptosis. Since all currently used general anesthetics modulate GABA and/or NMDA receptor systems at clinically relevant concentrations and all of them impair some important aspects of developmental synaptogenesis, it is hypothesized herein that general anesthetics with different cellular targets, i.e., T-channels, lack the neurotoxic potential frequently described with presently available anesthetics.

All currently used general anesthetics impair some important aspects of developmental synaptogenesis and yet they are a necessity in daily clinical practice. We think that rational and systematic development of safer anesthetics based on previously unrecognized cellular targets is justified and could be the best strategy for addressing the conundrum posed by anesthesia-induced developmental neurotoxicity.

Results

To begin to assess the safety of anesthetic steroid analogs with T-channel blocking activity, we compared 3β-OH with ketamine, a clinically used anesthetic known to cause significant developmental neurotoxicity in several mammalian species (e.g. rats, mice, monkeys). Since repeated ketamine administrations (every hour for total of six doses) at 20 or 40 mg/kg, i.p. have been reported to induce significant widespread neuroapoptotic degeneration in PND7 rat pups, we first determined the equipotent doses for 3β-OH based on LORR experiments.

Figure 10:
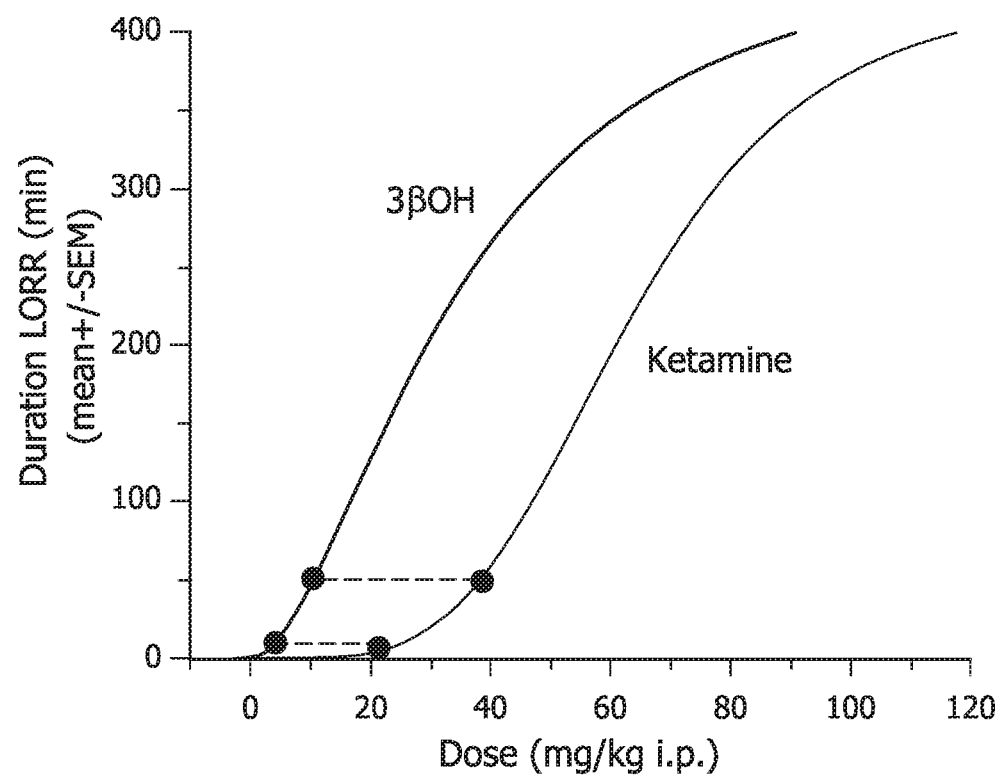
FIG. 10. Graphically shows that a 5 mg dose of 3β-OH is equipotent to a 20 mg dose of ketamine when tested by measuring LORR.

As shown in FIG. 10, the equipotent single dose of 3β-OH comparable to a lower dose of ketamine (20 mg/kg) was 5 mg/kg, i.p. whereas the equipotent dose of 3β-OH comparable to a higher dose of ketamine (40 mg/kg) was 10 mg/kg, i.p. When we performed serial analyses of several most vulnerable brain regions (e.g. hippocampus-CA1-subiculum junction, two anterior thalamic nuclei and cingulate cortex) by staining for activated caspase-3, a sensitive indicator of apoptotic activation, we discovered that unlike repeated injections of ketamine at 20 mg/kg, repeated injections of 3β-OH (every hour for total of six doses), at equipotent dose of 5 mg/kg did not cause significant apoptotic activation as compared with vehicle in any of the examined brain regions (FIG. 11) except in subiculum. Moreover, compared with 3β-OH, ketamine-induced caspase-3 activation was significantly higher in all brain regions (*, p<0.05) (n=3-6 pups per data point). We concluded based on these pilot data that 3β-OH is significantly less neurotoxic to the developing brain than ketamine. Since the comparison between the two vehicles, cyclodextrin and saline did not yield any significant difference in caspase-3 activation in the examined brain regions the findings were combined and presented as a 'vehicle'.

Figure 11:
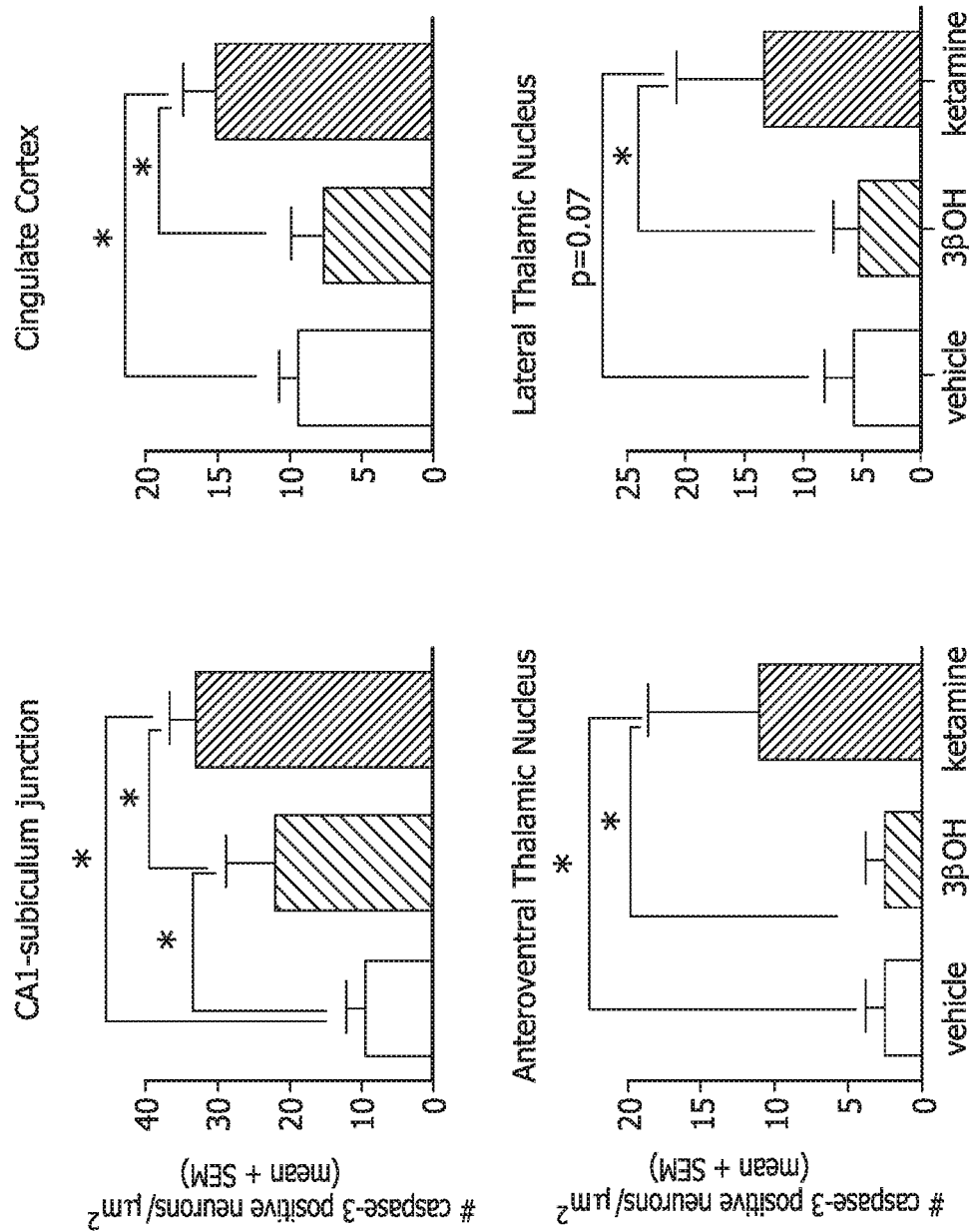
FIG. 11, depicting four graphs (two upper and two lower), shows that 3β-OH causes significantly less apoptotic activation relative to ketamine and that it is significantly less neurotoxic than ketamine to the developing brain (based on examination of brain sections).
Figure 12:
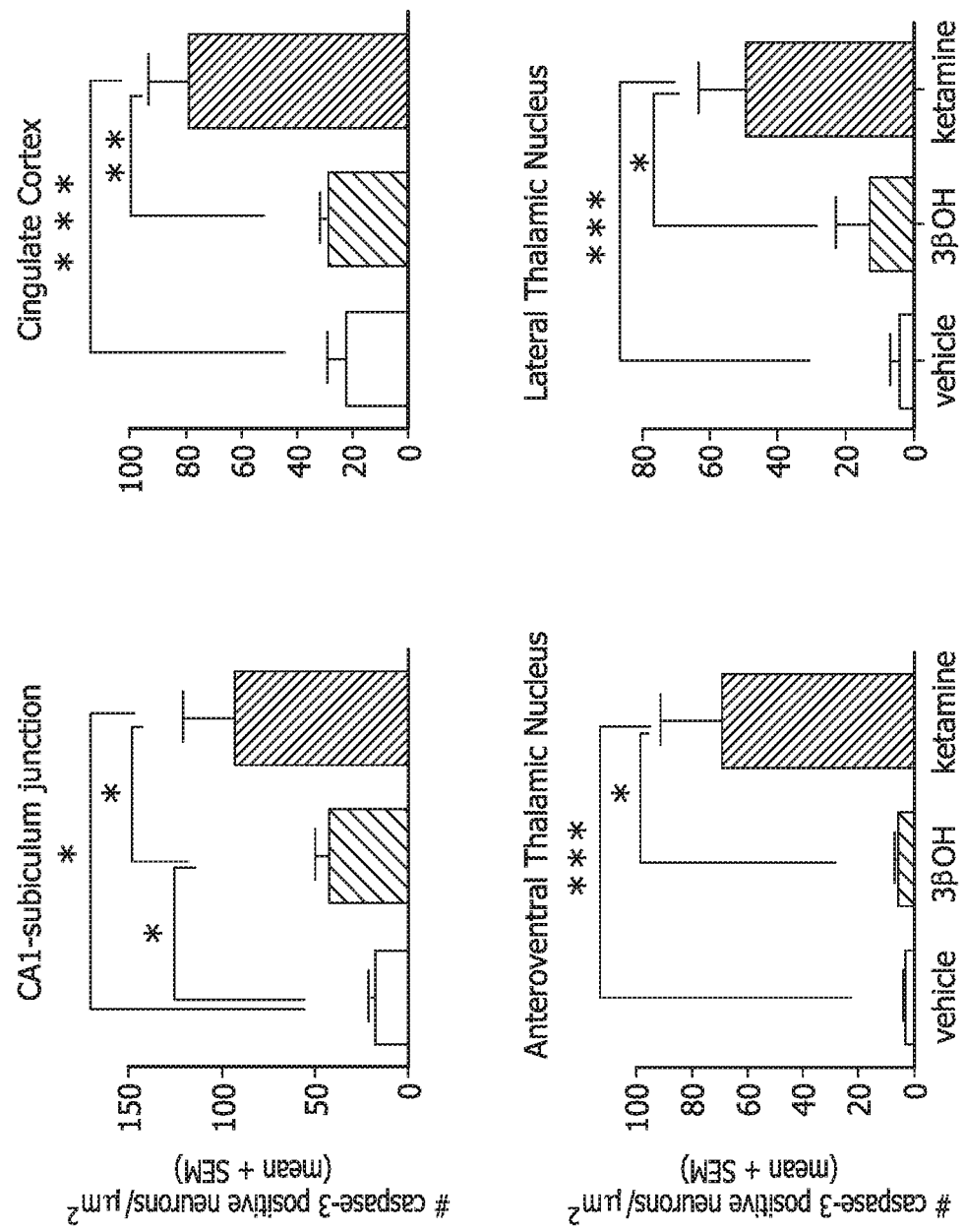
FIG. 12, depicting four graphs (two upper and two lower), demonstrates that, relative to the experiments of FIG. 11, even higher doses of 3β-OH still cause significantly less apoptotic activation that ketamine.

To examine whether a higher dose of 3β-OH could be potentially neurotoxic we administered repeatedly (6 doses hourly for total of 6 hours as described previously) the higher equipotent dose of either 10 mg/kg, i.p. of 3β-OH or 40 mg/kg i.p. of ketamine. As shown in FIG. 12 the higher dose of ketamine induced 3- to 6-fold increase in caspase-3 activation in vulnerable brain regions as compared with a twice lower dose (FIG. 11). However, twice higher dose of 3β-OH caused a small increase in caspase-3 activation compared with its lower dose, and the number of caspase-3 stained neurons remained significantly lower than the higher dose of ketamine (*, p<0.05; **, p<0.01). Interestingly, in all examined brain regions, except for subiculum, there was no significant increase in caspase-3 activation when the higher dose of 3β-OH was compared with vehicle whereas there was a significant increase when the higher dose of ketamine was compared with vehicle (*, p<0.05; ***, p<0.01) (n=3-6 pups per data point). Since the comparison between the two vehicles, cyclodextrin and saline did not yield any significant difference in caspase-3 activation in the examined brain regions the findings were combined and presented as a 'vehicle'. Based on these pilot findings, we conclude that 3β-OH is substantially less neurotoxic compared with ketamine, i.e. even at a higher dose 3β-OH-induced caspase-3 activation was similar to a vehicle (with the exception of subiculum).

3. Long-Term Functional Outcomes of an Early Exposure to T-Channel Blocking Neuroactive Steroid Analogs.

Background: Our first report over a decade ago (Jevtovic-Todorovic et al., 2003) revealed that exposure of animals to commonly used general anesthetics at the peak of their developmental synaptogenesis could be detrimental to their cognitive and social development. Anesthetics are now viewed as possible neurotoxins for the immature brain with potential to cause long-lasting alterations in behavior. The concern gained momentum when certain aspects of impaired cognitive and social behaviors in humans were linked to anesthesia exposure during early stages of postnatal life. The cognitive gap that was noted during childhood was shown to widen in adolescence and young adulthood (Jevtovic-Todorovic et al., 2003) when those exposed to early anesthesia were compared with controls, presumably due to the impairment of higher neurocognitive functions often referred to as 'executive' functions.

However, a causative link between electrophysiological and behavioral impairments and potentiation of GABAergic or inhibition of NMDA neurotransmitter systems has not been confirmed. It would be difficult to establish such a link considering the fairly promiscuous nature of currently available anesthetics, which are known to modulate other cellular targets (e.g. leak potassium channels, GABA and glutamate transporters to name a few).

Results

Without wishing to be bound by any particular theory, we hypothesize herein that steroid analogs with T-channel blocking properties function as general anesthetics but lack the neurotoxic potential observed with presently available anesthetics and will not cause long-term impairments in synaptic neurotransmission and behavioral development.

Figure 13A:
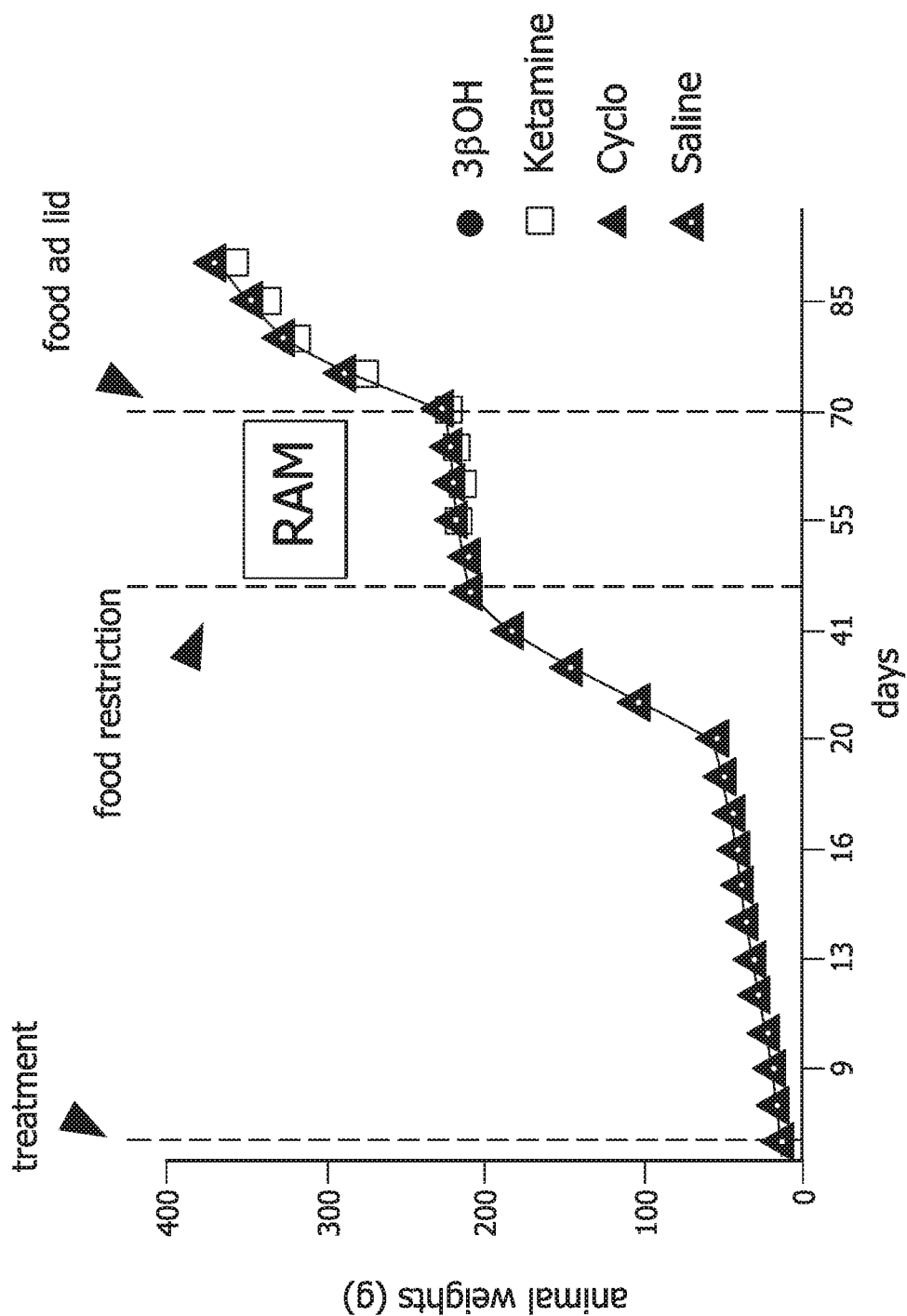
FIG. 13, comprising A, B, and C, graphically depicts the results of experiments demonstrating that early exposure to 3β-OH does not cause long-term impairments in learning and memory.
Figure 13B:
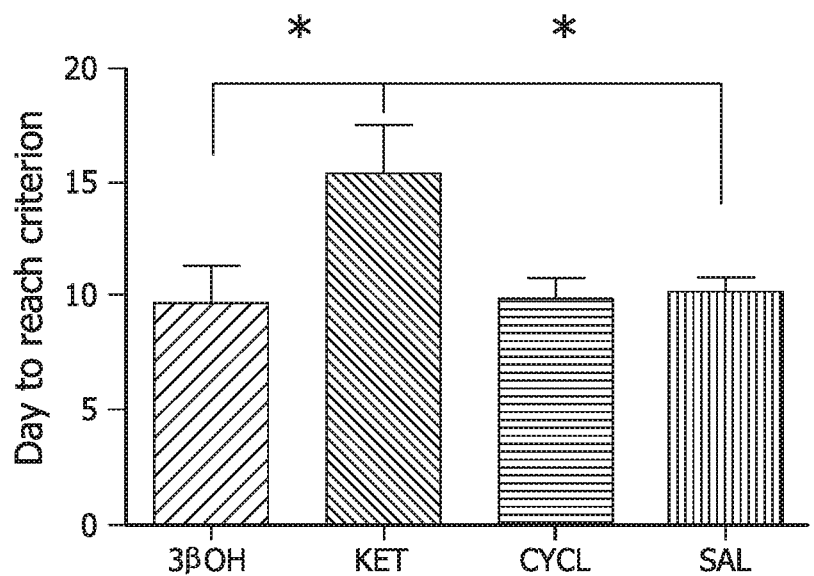

An early exposure to 3β-OH does not cause long-term impairments in learning and memory. To assess cognitive abilities of our rats we tested their spatial working memory using the 8-arm radial arm maze test (RAM). We began by comparing the overall appearance and daily weight of rats in each group (saline, cyclodextrin, 3β-OH at 10 mg/kg and ketamine at 40 mg/kg) since nutritional status and general state of health are critically important for cognitive development. Based on their general appearance, rats in different groups could not be distinguished from each other. Similarly, there was no difference in daily weight gain among the groups (FIG. 13A). The time points when the animals were treated (PND 7), food restricted (from PND 45), tested on the RAM (from PND 53) and permitted to eat ad libitum (from PND 70) are indicated on the graph. Food restriction, a necessary component of the RAM learning protocol, was limited so that no rat lost more than 10%-15% of its body weight. Ketamine-treated rats were significantly impaired relative to saline controls (*, $p<0.05$) in terms of days required to reach a criterion demonstrating learning (8 correct responses out of the first 9 responses for 4 consecutive days) (FIG. 13B). Compared with rats in the ketamine-treated group, those in the 3β-OH group showed a significant decrease in the number of days required to reach criterion (*, $p<0.05$), a finding that was indistinguishable from vehicle animals (saline and cyclodextrin), indicating that 3β-OH, unlike ketamine, does not impair the spatial learning in rats.

Figure 13C:
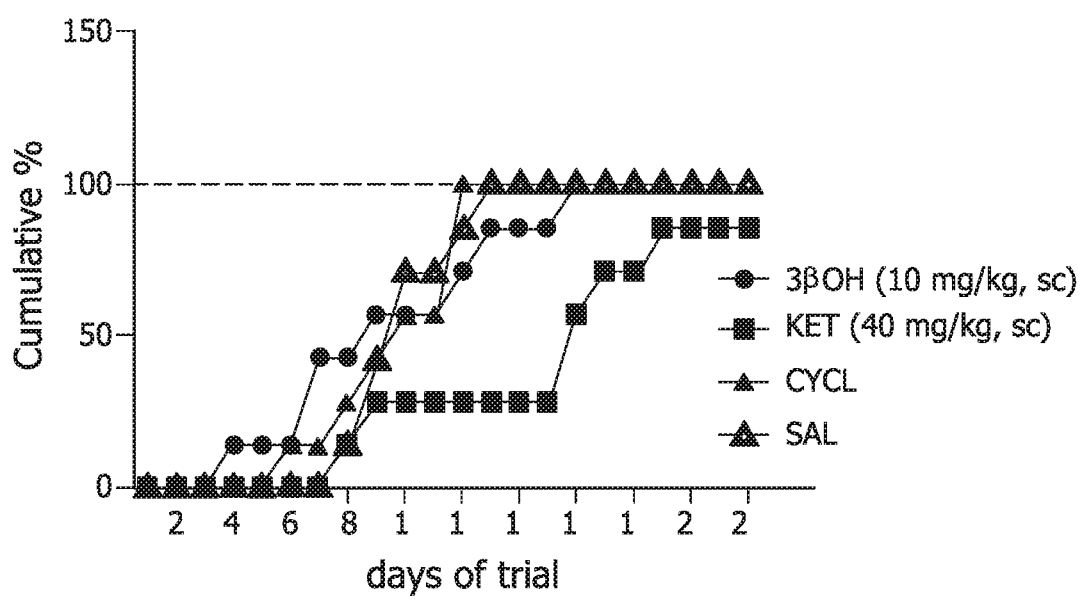

Graphing RAM data in terms of the cumulative percentage of rats reaching criterion as a function of days of trials (FIG. 13C) showed that the acquisition rate of the ketamine-treated group (blue squares) began to slow down as compared with that of saline controls (open triangles) by the 9th day and remained substantially slower for the remainder of training. In contrast, rats in the 3β-OH group (red circles) initially exhibited slightly faster acquisition than did those in the sham control groups (saline and cyclodextrin). However, their acquisition rate slowed down somewhat based on the fact that all the vehicle animals had mastered the task by the 13th day whereas 100% acquisition in the 3β-OH group did not occur until the 16th day, at which point their learning was identical to the learning curve of sham controls. While about 15% of ketamine-treated rats did not learn the task during the allotted time, all 3β-OH rats did so several days before the cut-off point and were practically indistinguishable from sham controls.

Figure 14:
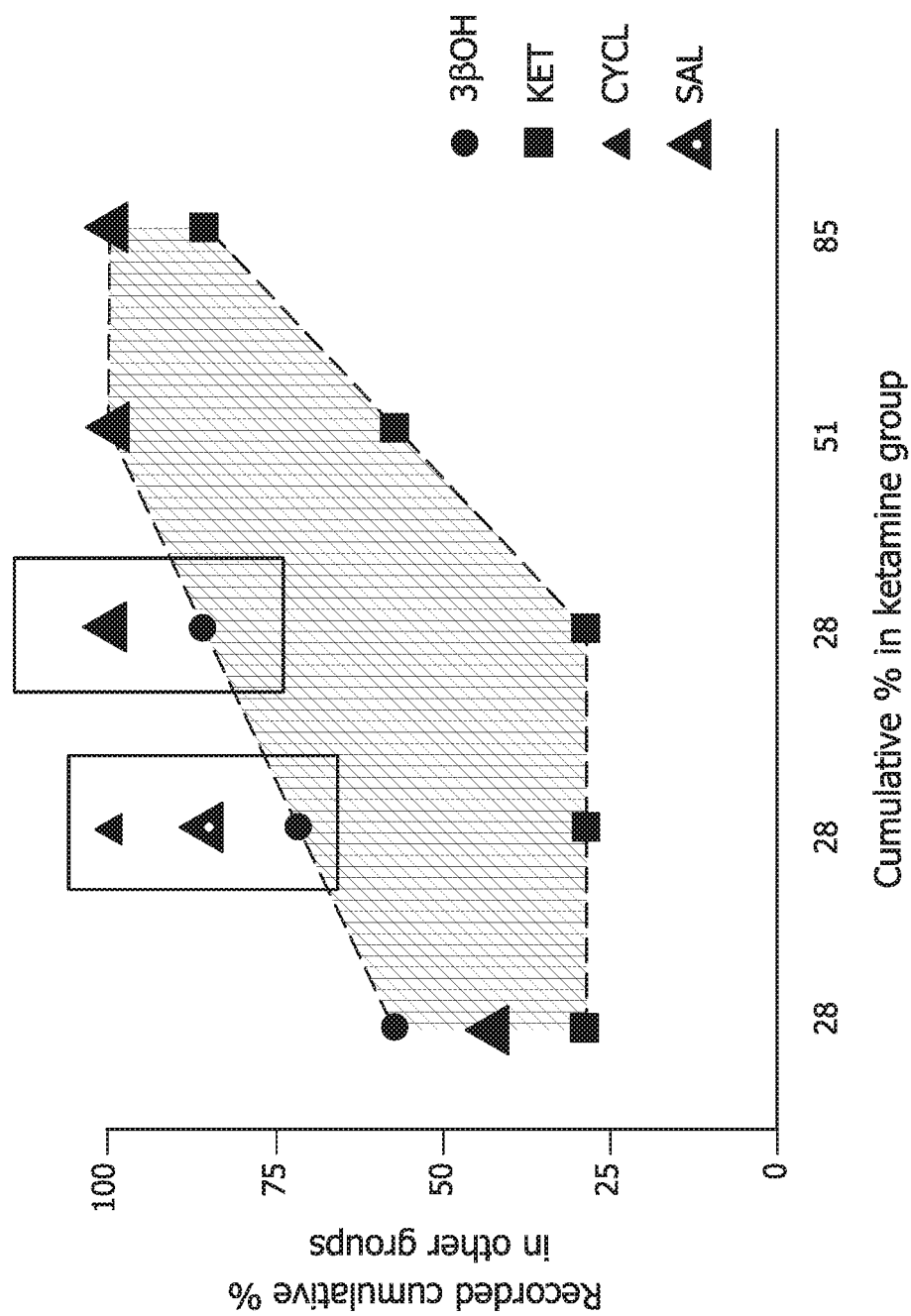
FIG. 14 graphically depicts the results of a comparison of 3β-OH to ketamine and vehicle groups when calculating cumulative percentages of rats reaching criterion, relative to the experiments as displayed in FIG. 13.

To further scrutinize how the acquisition rate of 3β-OH-treated rats compares to ketamine and vehicle groups, we plotted the cumulative percent scores for ketamine-treated animals relative to recorded cumulative percent scores for other groups, using a percent-percent plot (p-p plot) (FIG. 14). We found that when only 28% of ketamine-treated rats had reached criterion, roughly half of 3β-OH-treated ones and sham controls had mastered the task. While the learning curve of ketamine-treated rats remained flat, both 3β-OH-treated and vehicle controls showed steady improvement enabling animals to reach criterion (100%) while about 85% of ketamine animals managed to master the task in the allotted time. We conclude that 3β-OH anesthesia allows for spatial learning comparable to sham controls and significantly better than what is observed with ketamine. The learning behavior of 3β-OH-treated rats is similar to that of sham controls resulting in a large gap (shaded area) in learning ability between ketamine-treated (lower blue dotted line) and 3β-OH-treated animals (upper red dotted line). A slight slowing in the acquisition rate observed with 3β-OH-treated rats when compared to vehicle controls (saline—SAL and cyclodextrin—CYCL) during the mid-portion of training (as discussed in FIG. 13C) is highlighted with rectangles.

It should be noted that 3β-OH can reduce hyperalgesia for at least 48 hours after surgery (data not shown).

The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

While this invention has been disclosed with reference to specific embodiments, it is apparent that other embodiments and variations of this invention may be devised by others skilled in the art without departing from the true spirit and scope of the invention.

BIBLIOGRAPHY

Joksovic P M, Weiergraber M, Lee W Y, Struck H, Schneider T and Todorovic S M. Isoflurane-sensitive presynaptic R-type calcium channels contribute to inhibitory synaptic transmission in the rat thalamus. The Journal of Neuroscience 29(5):1434-1445, 2009.

Jevtovic-Todorovic V, Hartman R E, Izumi Y, Benshoff N D, Dikranian K, Zorumski C F, Olney J W, Wozniak D F (2003). Early exposure to common anesthetic agents causes widespread neurodegeneration in the developing rat brain and persistent learning deficits. J Neurosci 23(3):876-882.

Nelson M T, Joksovic P. M., Perez-Reyes E. and Todorovic S. M. The endogenous redox agent L-cysteine induces T-type Ca2+ channel-dependent sensitization of a novel subpopulation of rat peripheral nociceptors. The Journal of Neuroscience 25(38):8766-75, 2005.

Todorovic, S M. Pathirathna, S., Brimelow, B. C., M. M. Jagodic, S-H, Ko, Jiang, X., Nilsson, K. R., Mennerick, S., Zorumski, C. F., Covey, D. F. and Jevtovic-Todorovic, V. 5β-reduced neuroactive steroids are novel voltage-dependent blockers of T-type Ca2+ channels in rat sensory neurons in vitro and potent peripheral analgesics in vivo. Molecular Pharmacology 66(5):1223-1235, 2004.

Todorovic, S M and Jevtovic-Todorovic, V. Neuropathic pain: Role of presynaptic T-type channels in nociceptive signaling. Pflugers Archiv—European Journal of Physiology, 2013, 465(7):921-7.

Wilder R T, Flick R P, Sprung J, Katusic S K, Barbaresi W J, Mickelson C, Gleich S J, Schroeder D R, Weaver A L, Warner D O (2009). Early exposure to anesthesia and learning disabilities in a population-based birth cohort. Anesthesiology 110(4):796-804.

Han et al. (J. Med. Chem., 1996, 39 (21), pp 4218-4232).

Paradiso et al. (Molecular Pharmacology Aug. 1, 2000 vol. 58 no. 2 341-351).

Ayoola et al., Psychopharmacology (Berl). 2014 September; 231(17):3503-15. doi: 10.1007/s00213-014-3588-0. Epub 2014 May 7.

Latham et al., Diabetes. 2009 November; 58(11):2656-65. doi: 10.2337/db08-1763. Epub 2009 Aug. 3.

Obradovic et al., 2014, PLoS ONE 9(4): e91467. doi: 10.1371/journal.pone.0091467.

Jevtovic-Todorovic, V. and Olney, J W, 2008, Anesthesia and Analgesia, 106:6:1659.

Messinger, R. B., et al., 2009, Pain, 145(1-2):184.

What is claimed is:

1. A method for anesthetizing a pediatric subject and reducing the risk of neurotoxicity and of impairing developmental synaptogenesis associated with a neurotoxic general anesthetic, said method comprising administering to said subject an effective amount of a neuroactive steroid analgesic, wherein said neuroactive steroid analgesic has reduced neurotoxicity compared to said neurotoxic general anesthetic, wherein said neuroactive steroid analgesic is (3β,5β,17β)-3-hydroxyandrostane-17-carbonitrile (3β-OH) and is administered at a dose ranging from about 5 mg/kg/body weight to about 25 mg/kg body weight, thereby anesthetizing said subject and reducing the risk of neurotoxicity and of impairing developmental synaptogenesis associated with said neurotoxic general anesthetic.

2. The method of claim 1, wherein said 3β-OH:
   a. inhibits low voltage activated T-channel activity;
   b. inhibits low voltage activated R-channel activity;
   c. inhibits the ability to feel pain and partially or completely reduces loss of sensation;
   d. does not cause long-term impairments in synaptic neurotransmission;
   e. does not cause long-term impairments in behavioral development;
   f. reduces the risk in pediatric subjects of long-term behavioral impairment and impaired cognitive development compared to the long-term behavioral impairment and impaired cognitive development resulting from use of a neurotoxic general anesthetic; and
   g. has reduced neurotoxicity activity relative to other anesthetics.

3. The method of claim 2, wherein said low voltage activated T-channel is $Ca_v3.2$ and said low voltage activated R-channel is $Ca_v2.3$.

4. The method of claim 1, wherein said method does not cause long-term impairment of memory.

5. The method of claim 1, wherein said method does not cause long-term impairment of learning.

6. The method of claim 1, wherein said 3β-OH induces analgesia.

7. The method of claim 1, wherein said 3β-OH is administered intravenously or by inhalation.

8. The method of claim 1, wherein said method inhibits perioperative pain.

9. The method of claim 1, wherein said method inhibits post-operative pain.

10. The method of claim 1, wherein said method inhibits development of hyperalgesia.

* * * * *